United States Patent
Emadi et al.

(10) Patent No.: US 9,925,561 B2
(45) Date of Patent: Mar. 27, 2018

(54) CAPACITIVE MICROMACHINED ULTRASONIC TRANSDUCER WITH MULTIPLE DEFLECTABLE MEMBRANES

(71) Applicant: UNIVERSITY OF MANITOBA, Winnipeg, Manitoba (CA)

(72) Inventors: Tahereh Arezoo Emadi, Manitoba (CA); Douglas A. Buchanan, Manitoba (CA)

(73) Assignee: THE UNIVERSITY OF MANITOBA, Winnipeg, Manitoba (CA)

( * ) Notice: Subject to any disclaimer, the term of this patent is extended or adjusted under 35 U.S.C. 154(b) by 252 days.

(21) Appl. No.: 14/772,517

(22) PCT Filed: Mar. 3, 2014

(86) PCT No.: PCT/CA2014/050162
§ 371 (c)(1),
(2) Date: Sep. 3, 2015

(87) PCT Pub. No.: WO2014/134723
PCT Pub. Date: Sep. 12, 2014

(65) Prior Publication Data
US 2016/0016198 A1 Jan. 21, 2016

Related U.S. Application Data

(60) Provisional application No. 61/772,651, filed on Mar. 5, 2013.

(51) Int. Cl.
*B06B 1/02* (2006.01)
*A61B 8/00* (2006.01)
(Continued)

(52) U.S. Cl.
CPC .......... *B06B 1/0292* (2013.01); *A61B 8/4483* (2013.01); *G01D 5/2417* (2013.01); *G01H 11/06* (2013.01)

(58) Field of Classification Search
CPC ..... B06B 1/0292; G01H 11/06; A61B 8/4483; G01D 5/2417
See application file for complete search history.

(56) References Cited

U.S. PATENT DOCUMENTS 8,381,594 B2 * 2/2013 Adachi .................... A61B 8/00
367/92
2010/0173437 A1 7/2010 Wygant et al.
(Continued)

FOREIGN PATENT DOCUMENTS

WO 2010097729 A 9/2010

OTHER PUBLICATIONS

T. L. Szabo, "Diagnostic Ultrasound Imaging—Inside Out", Elsver Academic Press, 2004.
(Continued)

*Primary Examiner* — Daniel Pihulic
(74) *Attorney, Agent, or Firm* — William J. Clemens; Shumaker, Loop & Kendrick, LLP

(57) ABSTRACT

A capacitive micromachined ultrasonic transducer (CMUT) having at least two deflectable membranes. The membranes are spaced from each other, and the membranes contribute to and/or are responsive to receive or transmit an ultrasonic signal. Spacing between the at least two deflectable membranes is adjustable through application of a voltage to cause deflection of at least one of the deflectable membranes, to affect the receive/transmit properties of the CMUT.

20 Claims, 30 Drawing Sheets

(51) Int. Cl.
  *G01H 11/06* (2006.01)
  *G01D 5/241* (2006.01)

(56) References Cited

U.S. PATENT DOCUMENTS

| | | | | |
|---|---|---|---|---|
| 2010/0251823 | A1* | 10/2010 | Adachi | A61B 8/00 73/606 |
| 2011/0040189 | A1* | 2/2011 | Petruzzello | B06B 1/0292 600/459 |
| 2013/0135970 | A1* | 5/2013 | Ngo | H04B 11/00 367/137 |
| 2016/0016198 | A1* | 1/2016 | Emadi | B06B 1/0292 367/7 |

OTHER PUBLICATIONS

G. Thomas, D. Flores-Tapia, S. Pistorius, N. Fernando, "Synthetic Aperture Ultrasound Imaging of XLPE Insulation of Underground Power Cables", IEEE Electrical Insulation Magazine, vol. 26, No. 34, pp. 24-34, 2010.

M. Crocco, P. Pellegretti, C. Sciallero A. Trucco, "Combining Multi-Pulse Excitation and Chirp Coding in Contrast-Enhanced Ultrasound Imaging", Measurements Science and Technology, vol. 20, 104017, 2009.

A. S. Logan, J. T. W. Yeow, "Fabricating Capacitive Micromachined Ultrasonic Transducers with a Novel Silicon-Nitride-Based Wafer Bonding Process", IEEE Transactions on Ultrasonics, and Frequency Control, vol. 56, No. 5, pp. 1074-1084, 2009.

B. T. Khuri-Yakub, O. Oralkon, M. Kupnik, "Next-Gen Ultrasound", IEEE Spectrum, vol. 46, No. 5, pp. 44-54, 2009.

P. Zhang, G. Fitzpatric, W. Moussa, R. J. Zemp, "CMUTs with Improved Electrical Safety & Minimal Dielectric Surface Charging", in Proc. IEEE Ultrasonics Symposium, San Diego, CA, pp. 1881-1885, 2010.

T. A. Emadi, G. Thomas, S. Pistorius, D. A. Buchanan, "Design and Analysis of a Wide Bandwidth Immersion MEMS Transducer Array for Fault Detection in Power Cables," IEEE Sensors, Taipei, Taiwan, Oct. 2012.

T. A. Emadi, G. Thomas, S. Pistorius, D. A. Buchanan, "Capacitive Micromachined Ultrasonic Transducer Array with Pencil Beam Shape and Wide Range Beam Steering," The 26th Conference on Solid-State Transducers, Eurosensors, Krakow, Poland, Sep. 2012.

O. Oralkon, A. S. Ergun, J. A. Jhonson, M. Karaman, U. Demirci, K. Kaviani, T. H. Lee, B. T. Khuri-Yahub, "Capacitive Micromachined Ultrasonic Transducers: Next-Generation Arrays for Acoustic Imaging?", IEEE Transaction on Ultrasonics, Ferroelectrics, and Frequency Control, vol. 49, No. 11, pp. 1596-1610, 2002.

W. You, E. Cretu, R. Rohling, M. Cai, "Tiltable Ultrasonic Transducers: Concept, Beamforming Methods and Simulation," IEEE Sensors Journal, vol. 11, No. 10, pp. 2286-2300, 2011.

L.L. Liu, O.M. Mukdadi, C.F. Herrmann, R.A. Saravanan, J.R. Hertzberg, S.M. George, V.M. Bright, R. Shandas, "A Novel Method for Fabricating Micromachined Ultrasonic Transducers with Ultra-Thin Membranes," IEEE Ultrasonics Symposium, pp. 497-500, 2004.

MEMSCAP, www.memscap.com/products/mumps/polymumps.
COMSOL, http://www.comsol.com/.

* cited by examiner

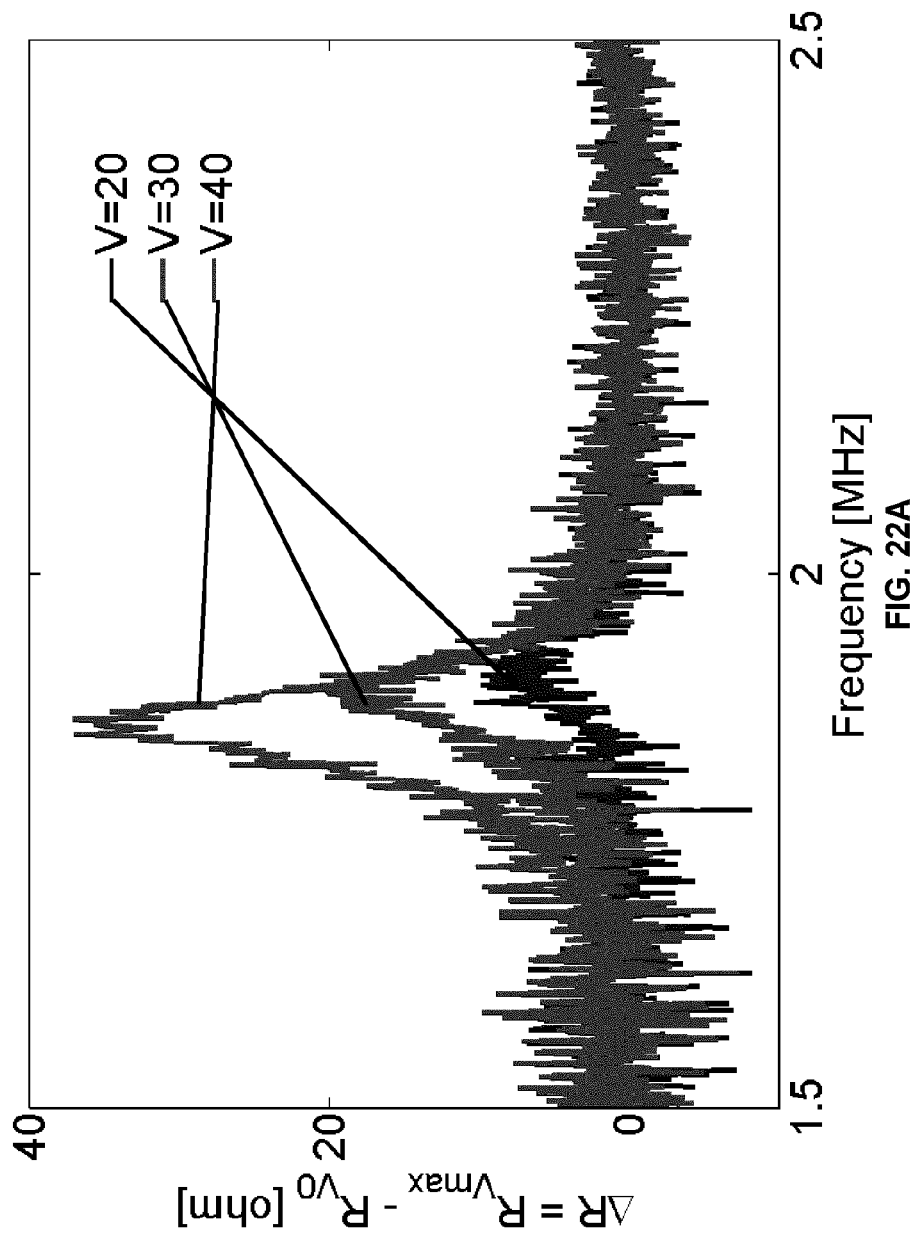

CAPACITIVE MICROMACHINED ULTRASONIC TRANSDUCER WITH MULTIPLE DEFLECTABLE MEMBRANES

REFERENCE TO RELATED APPLICATION

The present disclosure claims priority from U.S. provisional patent application No. 61/772,651 filed Mar. 5, 2013, the entirety of which is hereby incorporated by reference.

TECHNICAL FIELD

The present disclosure relates generally to capacitive micromachined ultrasonic transducers and methods of fabrication thereof.

BACKGROUND

Ultrasound technology may be commonly used for the purpose of detection and location of various objects [1], such as for fault detection in underground cables [2] and for medical imaging [3]. A common approach in imaging objects is to employ conventional piezoelectric transducers. However, piezoelectric transducers may have drawbacks that limit their applications, such as poor acoustic matching, dimensional limitation, temperature dependence, narrow bandwidth, and/or limited uniformity arising from fabrication difficulties. With the help of microfabrication techniques, microelectromechanical system (MEMS)-based ultrasound transducers have been introduced as an alternative to piezoelectric transducers [4, 5]. These devices, also known as capacitive micromachined ultrasonic transducers (CMUTs), may provide one or more advantages over traditional transducers. For example, they may offer wider bandwidth, better acoustic matching, higher sensitivity, highly miniaturized system, ability to produce large and uniform arrays with different number of cells, improved electrical safety, temperature independent properties, effective beam steering, and/or the potential for mass fabrication [5-9].

However, MEMS-based ultrasonic devices may still exhibit drawbacks, such as high driving voltage requirements, safety issues, and/or cavity and insulating layer breakdown due to the large electric field. Moreover, demands for high resolution imaging may result in a desire for generating even higher acoustic power and pressure, especially for imaging complex geometries such as multi-layer underground power cable. Higher sensitivity may also be desirable when operating in receiving mode, since the reflected wave can be weakened due to the wave passing through several layers of different material, as well as the distance of the object.

SUMMARY

In some examples, the present disclosure provides a capacitive micromachined ultrasonic transducer (CMUT) including: at least two deflectable membranes; each of the at least two deflectable membranes being spaced from each other; the at least two deflectable membranes contributing to and/or being responsive to receive or transmit an ultrasonic signal; and spacing between the at least two deflectable membranes being adjustable through application of a voltage to cause deflection of at least one of the deflectable membranes, to affect the receive/transmit properties of the CMUT.

In some examples, the CMUT may include a static membrane spaced apart from the at least two deflectable membranes.

In some examples, the CMUT may include at least one electrical contact permitting electrical connection with at least a signal source, the at least one electrical contact being in electrical connection with at least one deflectable membrane.

In some examples, the CMUT may include at least a second electrical contact permitting electrical connection with a ground.

In some examples, the CMUT may include at least one support for spacing the at least two deflectable membranes from each other.

In some examples, the CMUT may include a substrate supporting the at least one support.

In some examples, the CMUT may include a substrate supporting at least one deflectable membrane.

In some examples, the at least one deflectable membrane may be anchored to the substrate.

In some examples, the at least one deflectable membrane may be anchored to the substrate via an intermediary support.

In some examples, there may be two deflectable membranes.

In some examples, the CMUT may include an insulator positioned to insulate at least one of the deflectable membranes from at least one other static or deflectable membrane or substrate.

In some examples, the CMUT may be fabricated using a sacrificial layer technique or a bonding process.

In some examples, the present disclosure provides a method of operating the CMUT described above, including: applying a respective DC biasing voltage to at least one of the deflectable membranes to space the at least one deflectable membrane at an initial separation from another deflectable membrane; and applying a respective AC driving voltage to at least a same or different one of the deflectable membrane.

In some examples, the method may include applying respective DC biasing voltages to each of the deflectable membranes to space the deflectable membranes at initial separations from each other; and applying respective AC driving voltages to each of the deflectable membranes.

In some examples, the DC biasing voltage applied to at least one deflectable membrane may be different from the DC biasing voltage applied to at least another one deflectable membrane.

In some examples, the AC driving voltage applied to at least one deflectable membrane may be different from the AC driving voltage applied to at least another one deflectable membrane.

In some examples, the respective DC biasing voltages may be selected to space the deflectable membranes at a selected separation from each other.

In some examples, the present disclosure provides a method of operating the CMUT described above, including: grounding an outermost of the deflectable membranes, the outermost deflectable being defined as the deflectable membrane contactable by an object external to the CMUT; and applying a DC biasing voltage and an AC driving voltage to at least one other deflectable membrane.

In some examples, the present disclosure provides an imaging transducer or a range sensor comprising the CMUT described above, for example comprising an array of a plurality of the CMUT described above.

BRIEF DESCRIPTION OF THE DRAWINGS

Reference will now be made to the drawings, which show by way of example embodiments of the present disclosure, and in which:

FIGS. 22A and 22B are charts showing the relative real part of the impedance versus frequency for examples of the disclosed CMUTs, having curved and flat anchor configurations.

It will be noted that throughout the appended drawings, like features are identified by like reference numerals.

DETAILED DESCRIPTION

The present disclosure provides examples for designing and developing semiconductor devices such as transducers and pressure sensors. Employing various suitable fabrication technologies, CMUTs (and sensors) may be developed utilizing two or more moving membranes. Such a design may be referred to as a Multi Moving Membrane CMUT ($M^3$-CMUT).

Example CMUT

Figure 3:
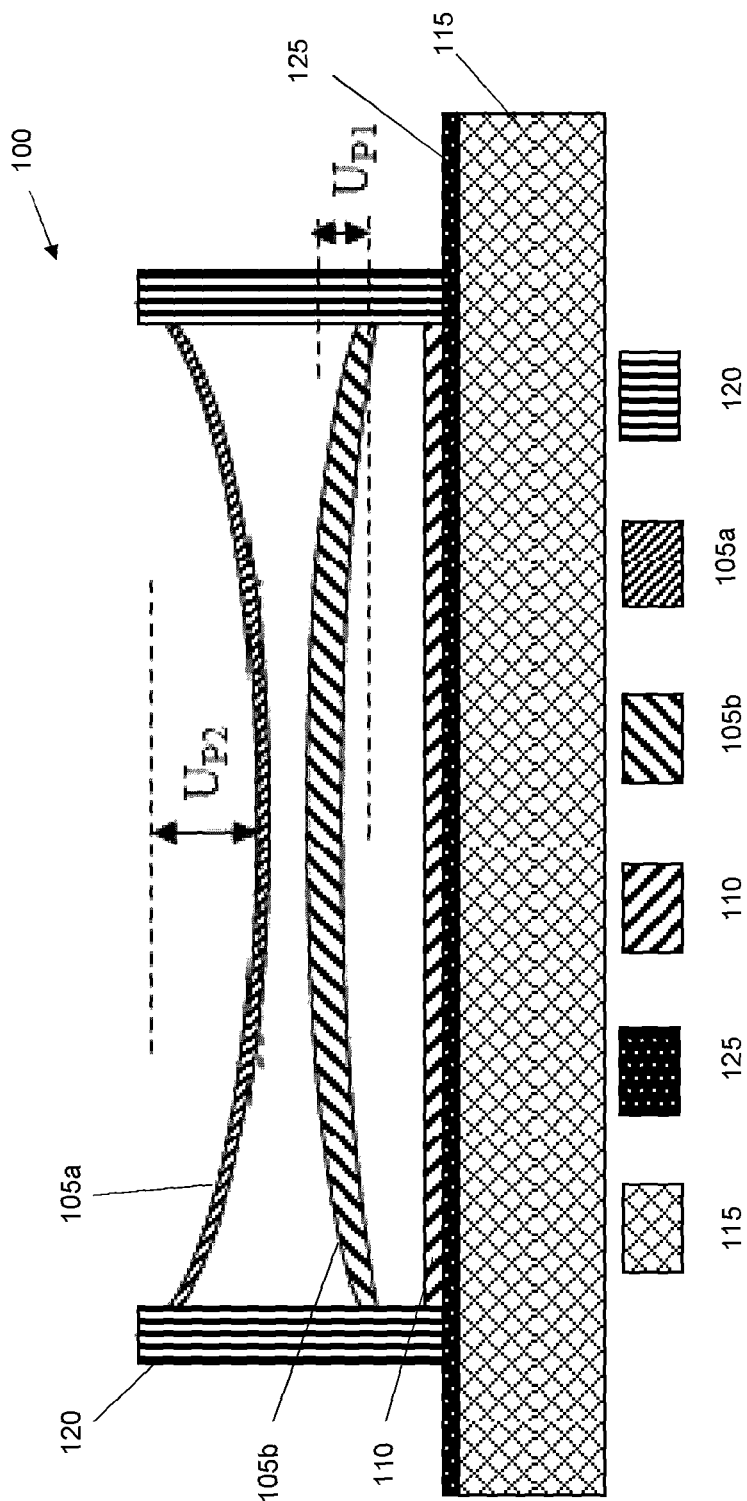
FIG. 3 is a schematic of an example of the disclosed CMUTs.

FIG. 3 is a schematic illustrating an example of the disclosed CMUTs, in this example including two deflectable membranes. Any suitable fabrication technique may be used, including, for example, Poly Multi-User MEMS Processes (PolyMUMPs™) and bonding techniques, as described further below.

In this example, the CMUT 100 includes two deflectable (or movable) membranes 105a, 105b (collectively and generally referred to as deflectable membranes 105) spaced apart from each other. In the example shown, the CMUT 100 also includes a static membrane 110, which may be fixed on and supported by a substrate 115. Although referred to as a "membrane", the static membrane 110 may not be deflectable and may not be flexible, unlike the deflectable membranes 105. One or more supports 120 may serve to suspend the deflectable membranes 105 and space them from each other. In some examples, the support(s) 120 may not be present, and the deflectable membranes 105 may be supported by other means (e.g., the deflectable membranes 105 may be self-supporting or may be supported by protrusions of the substrate 115).

The CMUT 100 may also include an insulator 125 for insulating the membranes 105, 110 from the substrate 115. In some examples, the CMUT 100 may not include a static membrane 110 and/or may not include a substrate 115. For example, the CMUT 100 may have two or more deflectable membranes 105 suspended by the support(s) 120 and spaced apart from each other (e.g., sufficiently spaced apart to allow for deflection of each membrane 105 independently), without any substrate 115 and/or without any static membrane 110. In other examples, the CMUT 100 may not include any substrate 115 and the bottom membrane may also be deflectable, such that the CMUT 100 has three deflectable membranes 105 and no static membrane 110. In some examples, one or more of the membranes 105, 110 may include an insulating material (e.g., an insulating coating or an insulator layer), in order to prevent shorting in the event that a deflectable membrane 105 is deflected into contact with another membrane 105, 110. In other examples, as described below, no insulation material may be needed.

In some examples, the substrate 115 may be made of silicon, and the insulator 125 may be made of silicon nitrate ($Si_3N_4$). The membranes 105, 110 may each be made of any suitable material, which may be a conductive material, such as polysilicon. In some examples, the membranes 105, 110 may include multiple materials, and may be a multi-layer such as a layer of conductive material and a layer of non-conductive material. The membranes 105, 110 may each be made of different materials. The deflectable membranes 105 may be made of a material with a sufficient amount of elasticity and/or flexibility, to permit deflection and/or vibration of the deflectable membranes 105. The support(s) 120 (where present) may be made of any suitable sufficiently rigid material, and may be electrically non-conductive, to avoid shorting out the CMUT 100.

Each membrane 105, 110 may serve as an electrical reference for its immediately adjacent neighbor(s). For example, in the example of FIG. 3, the middle deflectable membrane 105b may serve as an electrical reference for the upper deflectable membrane 105a and/or for the static membrane 110. Similarly, the upper deflectable membrane 105a may serve as an electrical reference for the middle deflectable membrane 105b. There may be more than two deflectable membranes 105, for example three or more deflectable membranes 105 may be suspended in a spaced-apart stack over each other in a manner similar to that shown in FIG. 3. In such an arrangement, each membrane 105, 110 may serve as an electrical reference for its immediately adjacent neighbor membrane(s) 105, 110.

Each of the membranes 105, 110 may be electrically conductive and may be driven with a bias voltage (typically a DC voltage) as well as an electrical signal (typically an AC voltage).

The polarity of the driving voltage on each membrane 105, 110 and/or the voltage differences between adjacent membranes 105, 110 define whether a given deflectable membrane 105 is pulled towards its neighboring membrane 105 (e.g., as shown in FIG. 3, the middle deflectable membrane 105b is drawn up towards the upper deflectable membrane 105a) or is pushed away from its neighboring membrane 105 (e.g., the middle deflectable membrane 105b may be drawn down towards the static membrane 110). Each membrane 105, 110 may be biased with appropriate voltage in order to exhibit a desired amount and direction of deflection in the deflectable membranes 105. Superimposed on such biased deflection, one or more of the deflectable membranes 105 may vibrate in response to application of an AC signal.

In some examples, a predefined stress (e.g., compressive or tensile stress) may be applied on a given deflectable membrane 105 in order to create a desired upward or downward deflection, prior to any biasing by the driving voltage.

The membranes 105, 110 may be individually connected to an electrical signal or ground (e.g., DC voltage, ground, or AC voltages at single or multiple frequencies, with an appropriate phase). In some examples, two or more membranes 105, 110 may be connected to the same electrical signal. Thus, each membrane 105, 110 may be biased to different selected voltages and/or different selected frequencies, or two or more membranes 105, 110 may have the same biasing voltage and/or frequency. In some examples, one or more of the membranes 105, 110 may be left "floating", that is not connected to any electrical signal or ground.

A plurality of individual CMUT 100 cells may be used to form 1-, 2-, and 3-D arrays, with different numbers of cells, different spacing, and different configurations, as appropriate.

The deflectable membranes 105 may each be individually fixed and/or be allowed to freely move (e.g., displace or vibrate) based on the desired application. The deflectable membranes 105 may be made of different materials (e.g., to alter the stiffness of the deflectable membranes 105 and therefore the resonant frequency of the CMUT 100), which may help to improve transducer properties, such as beam width and bandwidth. Two or more of the deflectable membranes 105 may also be made of the same or similar materials.

In some examples of the disclosed CMUTs 100, the required driving voltage for achieving a desired deflection of a deflectable membrane 105 may be reduced as compared to conventional single membrane CMUT designs. Similarly, for a given driving voltage, the deflection of a given deflectable membrane 105 may be greater in the disclosed CMUT 100 as compared to a conventional CMUT. Further, in the disclosed CMUT 100, deflection may be attained not only in the uppermost deflectable membrane (such as the upper deflectable membrane 105a in FIG. 3) but also other deflectable membranes (such as the middle deflectable membrane 105b in FIG. 3). Through selective application of biasing voltage and electrical signal, different deflectable membranes 105 may be selected to achieve different amplitudes of deflection.

The use of multiple deflectable membranes 105 may help to enhance one or more device properties and may help to address one or more CMUTs safety issues. In some examples, the uppermost membrane 105a may be grounded (e.g., where the CMUT 100 is in contact with an object of interest), while preserving the CMUT's 100 capability of vibrating with the same mode and shape as the biased condition. This may be useful in various applications, such as in health-related applications, for example, where the object of interest may be a patient's body, which again may be an approach for resolving the safety concerns. For example, where the CMUT 100 is intended to be used in contact against a patient's body, it may be desirable for the uppermost deflectable membrane 105a to be grounded and the bias voltage to be applied to the middle deflectable membrane 105b, so as to avoid exposing the patient to a potentially dangerous level of voltage (e.g., 135V bias voltage). Additionally, because a desired amount of deflection may be achieved with a lower bias voltage (as described further below), this may also increase the safety of the CMUT 100.

In some examples, the disclosed CMUT 100 may also exhibit enhanced sensitivity compared to conventional CMUTs, as the effective gap between two adjacent deflectable membranes 105 may be reduced by applying appropriate bias voltages to each deflectable membrane 105, for example. Reduction of the spacing between two adjacent deflectable membranes 105 may result in an increase in sensitivity of the CMUT 100. This may be useful for imaging complex geometries, for example, where the generated acoustic wave has to pass through several layers and the returning wave is also often weaker. The ability to adjust or tune the spacing between deflectable membranes 105 through adjusting the applied bias voltage may allow for the configuration and sensitivity of the CMUT 100 to be adjusted for different applications and/or dynamically during use. This may be useful in that a single CMUT design may be used for different applications requiring different membrane configurations and/or sensitivities.

Moreover, since each deflectable membrane 105 may be individually driven by independent electrical signals, each deflectable membrane 105 may be biased to vibrate at its own specific frequency and/or at its own amplitude as appropriate. For example, in the example of FIG. 3, the upper deflectable membrane 105a may vibrate with an amplitude of $U_{P2}$, while the middle deflectable membrane 105b may vibrate with an amplitude of $U_{P1}$, which may be greater or smaller than $U_{P2}$.

The direction of deflection of each deflectable membrane 105 may also be altered by adjusting or tuning the corresponding membrane bias voltage.

Example Methods of Fabrication

Micromachined transducers can be fabricated using various suitable microelectromechanical systems (MEMS) techniques. For example, they can be manufactured employing a sacrificial layer technique (e.g. Poly Multi-User MEMS Processes (PolyMUMPs™) process using polysilicon as the membrane material and silicon dioxide as the sacrificial layer [10]), using bonding technique (e.g. with a silicon nitride membrane [4]), utilizing Atomic Layer Deposition combined with diffusion bonding techniques [11], or using any other suitable technique.

Figure 1:
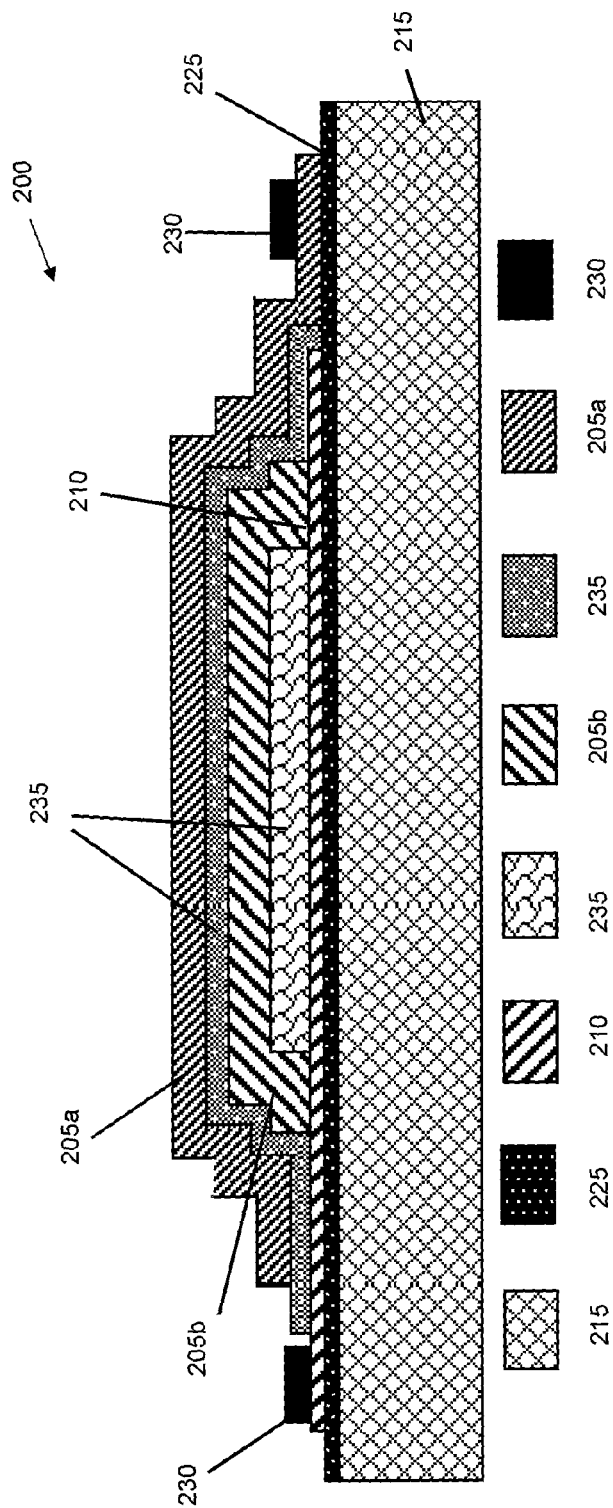
FIG. 1 is a schematic illustrating how an example of the disclosed CMUTs may be fabricated using an example sacrificial technique.

FIG. 1 is a schematic of a cross-sectional view of an example of the disclosed CMUT cell structure, during fabrication. In this example, the CMUT 200 may be fabricated on a substrate 215, such as a silicon substrate, and may be fabricated using a suitable sacrificial technique. The schematic shown in FIG. 1 may represent the CMUT 200 before the final release process.

This example CMUT 200 may include two deflectable membranes 205a, 205b (collectively and generally referred to as deflectable membranes 205) and a static membrane 210. As in the example of FIG. 3, the membranes 205, 210 may be made of any suitable material, such as a conductive material, and may be made of the same or different materials. The membranes 205, 210 may be made of multiple materials (e.g., a conductive layer coated with a non-conductive layer). In this example, each of the membranes 205, 210 may be made of a polysilicon material. There may be an insulator 225 (e.g., made of $Si_3N_4$ or other suitable non-conductive material) to insulate the membranes 105, 110 from the substrate 215. The CMUT 200 may include electrical contacts 230 for electrical communication with at least a ground and a signal source, for example. In some examples, the CMUT 200 may not include a ground contact. The electrical contacts 230 may be made of any suitable electrically conductive material, such as any metal (e.g., chromium and/or gold). In the example of FIG. 1, there may be an electrical contact 230 for connecting the middle deflectable membrane 205b and the static membrane 210 to a ground, and an electrical contact 230 for connecting the upper deflectable membrane 205a to a signal source. Similar to the configuration of FIG. 3, the CMUT 200 may not include any static membranes 210, may not include any substrate 215, and/or may not include any insulator 225.

FIG. 1 illustrates the CMUT 200 before release, in a sacrificial fabrication technique. The schematic includes sacrificial layers 235 (e.g., made of silicon dioxide, $SiO_2$) that will be removed (e.g., by etching or other suitable method) in order to achieve the final CMUT 200. Although not shown, one or more supports may be provided (e.g., may be provided as part of the fabrication process), in order to maintain spacing between the membranes 205, 210.

In this example, MEMSCAP™-PolyMUMPs [12] may be a suitable fabrication technology. Table I below lists examples of suitable materials and approximate layer thicknesses that may be used. Table I is provided as an illustrative example only, and the materials and/or thicknesses used may be varied.

TABLE I

| Layer | Material | Thickness [μm] |
| --- | --- | --- |
| Substrate | Silicon | N/A |
| Insulator | $Si_3N_4$ | 0.6 (±0.07) |

TABLE I-continued

| Layer | Material | Thickness [μm] |
| --- | --- | --- |
| Static membrane | Polysilicon (Poly0) | 0.5 (±0.03) |
| Sacrificial Layer | $SiO_2$ | 2.0 (±0.25) |
| Middle deflectable membrane | Polysilicon (Poly1) | 2.0 (±0.15) |
| Sacrificial Layer | $SiO_2$ | 0.75 (±0.08) |
| Upper deflectable membrane | Polysilicon (Poly2) | 1.5 (±0.1) |
| Contact | Cr and Au | 0.5Au and 0.05Cr (±0.06) |

In the example given in FIG. 1, the static membrane 210 and the middle deflectable membrane 205b may be designed to be grounded, while the upper deflectable membrane 205a may be driven with an AC electrical signal, which may be superimposed on a DC voltage (e.g., where a DC bias voltage is used).

A CMUT with any plurality of deflectable membranes may be implemented using the sacrificial technique or any other suitable technique, using any suitable materials and dimensions. For example, the disclosed CMUT, which may have individual cells and arrays, may be fabricated utilizing any suitable bonding technology, including fusion bonding or anodic bonding, among others.

Figure 2:
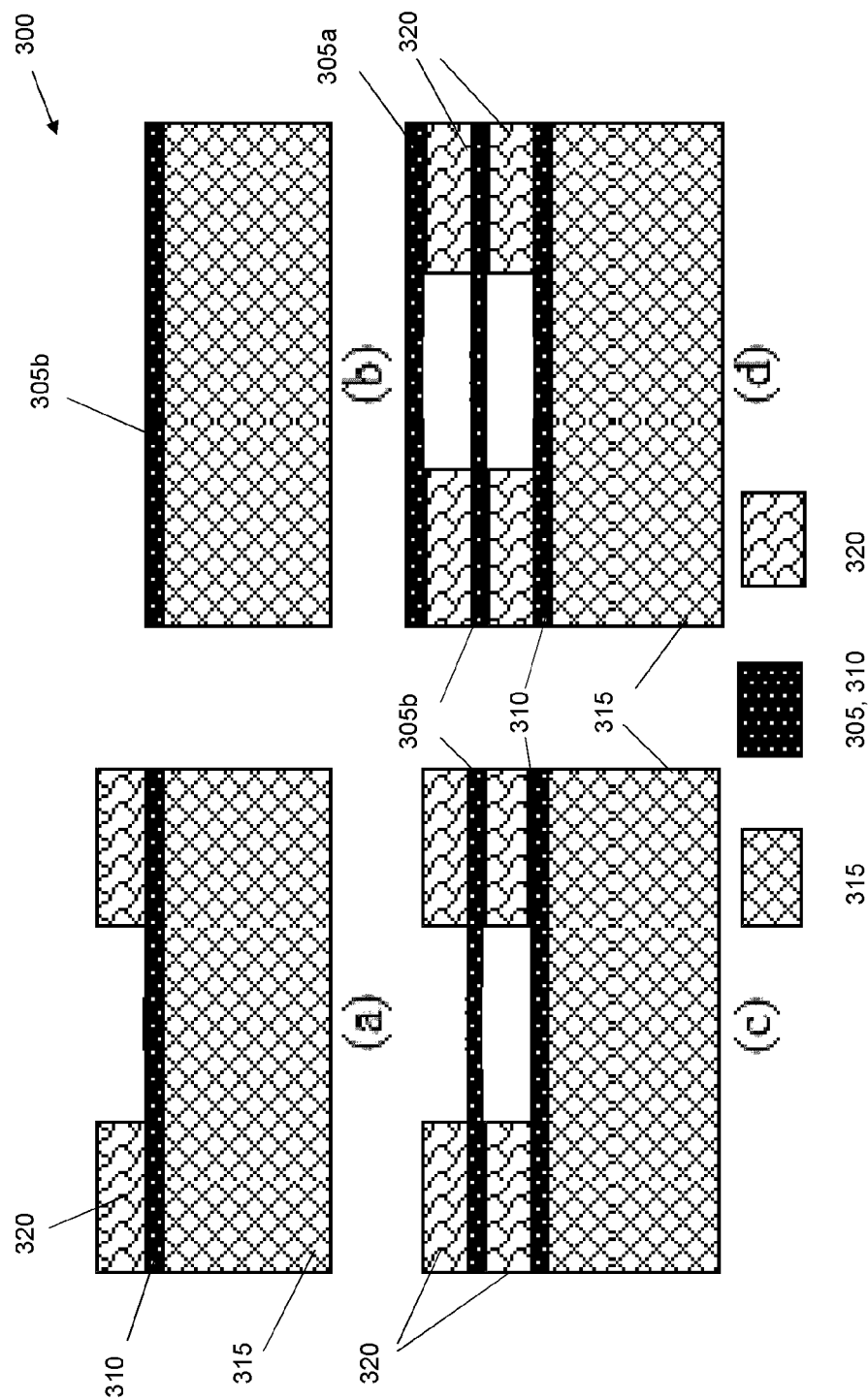
FIG. 2 is a schematic illustrating how an example of the disclosed CMUTs may be fabricated using an example bonding technique.

FIG. 2 is a schematic of a cross-sectional view of an example CMUT 300 being fabricated using an example bonding process. In this example, the CMUT 300 may include two deflectable membranes 305 (in this example, a middle deflectable membrane 305b and an upper deflectable membrane 305a) and a static membrane 310. A similar process may be used to fabricate CMUTs having more than two deflectable membranes 305. The example bonding process may include: a) forming the static membrane 310 on a substrate 315, along with supports 320; b) the middle deflectable membrane 305b may be initially provided on a second substrate (as a handling wafer) and c) bonded to the supports 320 (and the second substrate may then be removed) and further supports 320 may be added; then similarly d) the upper deflectable membrane 305a may be bonded. Contacts (not shown) may be added, to allow for electrical connection to an electrical signal and/or a ground. For example, the membranes 305, 310 may be fabricated to extend beyond on the supports 320 and be anchored on the substrate 315, where electrical contacts may be formed. Although not shown, there may also be an insulator to insulate the static membrane 310 from the substrate 315. Similar to the configuration of FIG. 3, the CMUT 300 may not include any static membranes 310, any substrate 315 (e.g., the substrate 315 may be etched away after fabrication), and/or any insulator.

In the example of FIG. 2, nitride may be used as the material for the membranes 305, 310, and silicon dioxide ($SiO_2$) may be used as the material for the supports 320. Other suitable materials may be used. For example, the membranes 305, 310 may be made of any suitable material, as described above, including metal oxide, polysilicon, or metal, among others.

Table II below lists example materials and approximate example layer thicknesses suitable for the example of FIG. 2.

TABLE II

| Layer | Material | Thickness [μm] |
| --- | --- | --- |
| Substrate | Silicon | N/A |
| Insulator | Nitride | 0.1 |

TABLE II-continued

| Layer | Material | Thickness [μm] |
|---|---|---|
| Structural Material | Oxide | 0.6 |
| Handling wafer | Si substrate with Nitride layer deposited thereon | 0.4 |
| Structural Material | Oxide | 0.6 |
| Handling wafer | Si substrate with Nitride layer deposited thereon | 0.4 |
| Contact | Cr and Au | 0.5Au and 0.05Cr |

The PolyMUMPs fabrication process from MEMSCAP may be used to develop transducers with membranes having any suitable radius, for example ranging from about 20 to about 80 μm.

In some examples, the fabrication methods may be adapted to fabricate CMUTs with a flat or a curved anchor configuration, as described below.

Figure 21A:
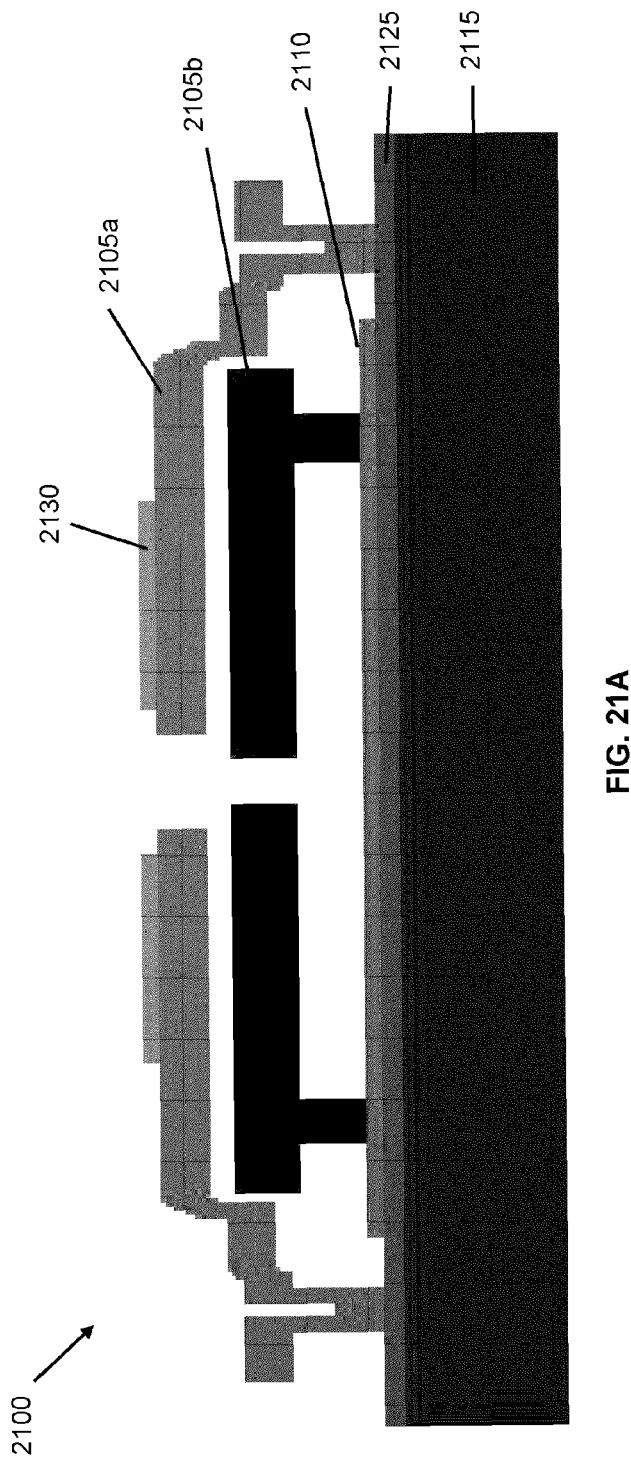
FIGS. 21A and 21B are schematic views of examples of the disclosed CMUTs, having curved anchor and flat anchor configurations.
Figure 21B:
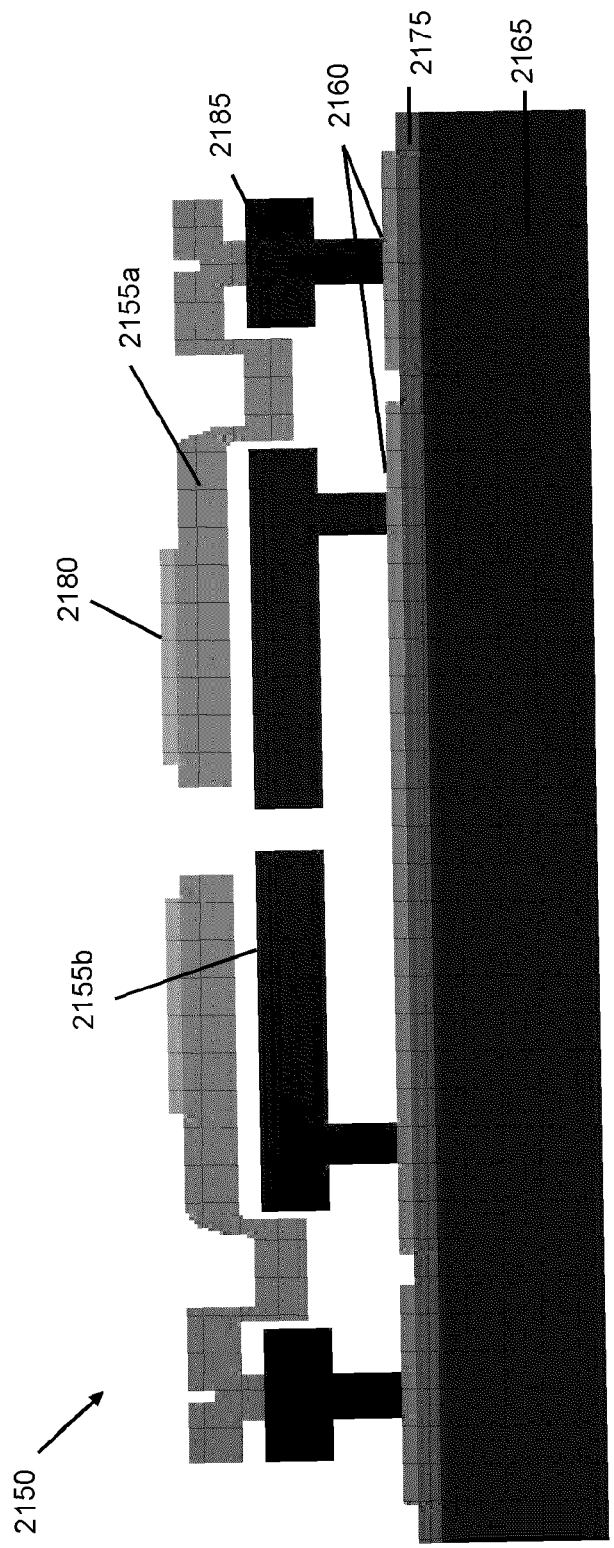

FIGS. 21A and 21B illustrate two examples 2100, 2150 of the disclosed CMUT devices that may be fabricated. Similar to the examples of the disclosed CMUTs 100, 200, 300 discussed above, the example CMUTs 2100, 2150 of FIGS. 21A and 21B may include an optional substrate 2115, 2165, which may be silicon); an optional static membrane 2110, 2160, which may be a conductive polymer material, such as polysilicon; an optional insulator 2125, 2175, which may be $Si_3N_4$; two or more deflectable membranes 2105 (individually 2105a, 2105b), 2155 (individually 2155a, 2155b), which may be a conductive polymer material, such as polysilicon; and one or more electrical contacts 2130, 2180, which may be gold. In these examples, the layer properties of the fabricated transducers 2100, 2150 may be as in Table I above. Material thicknesses and the sequence of the layers may be selected to suit the employed fabrication process, in this example PolyMUMPs.

The example CMUT 2100 of FIG. 21A is shown with a curved anchor configuration, in which the upper deflectable membrane 2105a is directly anchored to the substrate 2115 (or the insulator 2125) in a downwards extension or curve. The example CMUT 2150 of FIG. 21B is shown with a flat anchor configuration, in which the upper deflectable member 2155a is anchored onto an intermediary support 2185 (which may be fabricated as part of the fabrication of the middle deflectable member 2155b and may be made of the same polysilicon material), such that the upper deflectable member 2155a may be kept substantially flat or planar.

In the curved anchor configuration 2100, the upper deflectable membrane 2105a may be directly anchored to the insulator 2125 and/or substrate 2115 using a dry etching process that removes all the sacrificial layers during fabrication. This process may result in an upper deflectable membrane 2105a with curved edges as illustrated in FIG. 21A.

In the flat anchor configuration 2150, the intermediary support 2185 may be fabricated to form a protrusion on which the upper deflectable membrane 2155a may be anchored, which may result in a flatter (or substantially planar) membrane structure, as shown in FIG. 21B.

In both devices 2100, 2150, aside from the differences described above, the fabrication steps may be substantially similar, for example as described above. Any remaining sacrificial materials may be removed using any suitable techniques, such as using 49% HF followed by drying in $CO_2$.

Other fabrication techniques and materials may be suitable. For example, aside from sacrificial techniques and bonding processes, other MEMS fabrication techniques may be used. Fabrication techniques may be modified as appropriate, for example in order to fabricate more than two deflectable membranes.

Comparison with Conventional CMUTs

An example of the disclosed CMUT is now discussed in comparison with a conventional CMUT. In this comparison, the example CMUT 100 of FIG. 3 will be discussed, however it should be understood that this is illustrative only.

Figure 4:
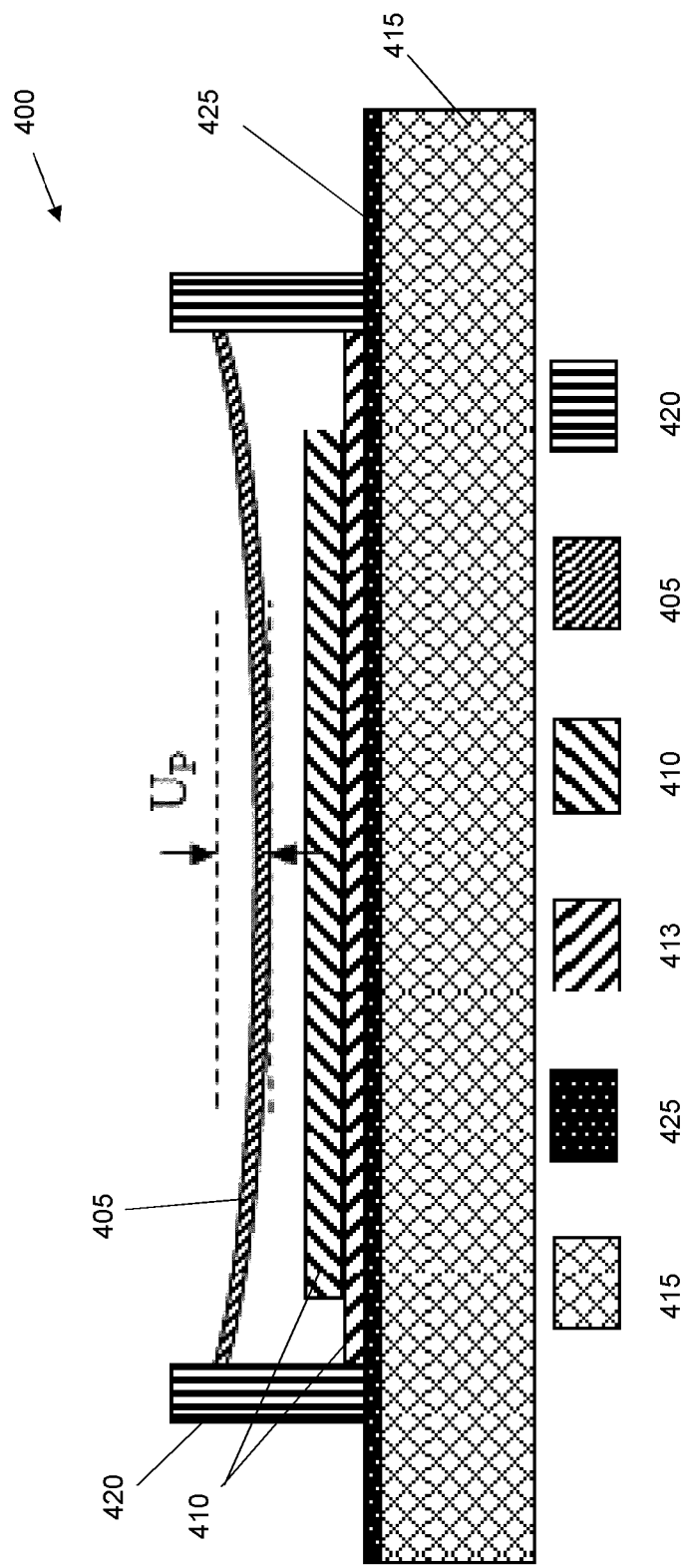
FIG. 4 is a schematic of an example conventional CMUT.

The example CMUT 100 of FIG. 3 may be fabricated using a sacrificial technique (e.g., as described with respect to FIG. 1), a bonding process (e.g., as described with respect to FIG. 2), or any other suitable methods, and using any suitable materials. For comparison, FIG. 4 illustrates a conventional CMUT 400, where the CMUT 400 includes only one deflectable polysilicon membrane 405. For this comparison, both the conventional CMUT 400 of FIG. 4 and the example disclosed CMUT 100 of FIG. 3 may comprise the layers listed in Table I, with the exception that the conventional CMUT 400 includes only one deflectable membrane 405. As shown in FIG. 4, the conventional CMUT 400 typically includes a bottom static electrode 410 supported by a substrate 415, and an insulator 425 between the bottom electrode 410 and the substrate 415. Depending on the employed fabrication technique and/or the design process, the single deflectable membrane 405 and/or the bottom electrode 410 may include one or more layers from similar or different materials. As an example, the bottom electrode 410 in FIG. 4 consists of two layers (e.g. two polysilicon layers with different thicknesses). The conventional CMUT 400 also typically includes supports 420 suspending the single deflectable membrane 405 over the bottom electrode 410.

In conventional CMUT devices, the bottom electrode 410 is typically grounded and there is only one deflectable membrane 405. Therefore, an applied DC bias voltage on the deflectable membrane 405 will tend to pull the deflectable membrane 405 toward the bottom electrode 410, and an applied AC signal with an angular frequency of w (which is typically close to the transducer's natural angular frequency) will tend to cause the deflectable membrane 405 to vibrate with the same frequency ω.

The disclosed multi-membrane CMUT 100 may operate on a similar principle. However, since there are multiple deflectable membranes 105 that are free to move and vibrate, each deflectable membrane 105 may be pulled towards or away from the static membrane 110 and towards or away from each other, depending on the voltage differences between each deflectable membrane 105 and its immediately adjacent membrane(s) 105, 110.

For comparison, COMSOL [13] electromechanics (emi) simulations have been conducted to investigate the operation of the example CMUT 100 of FIG. 3 and the conventional CMUT 400 of FIG. 4.

Figure 5:
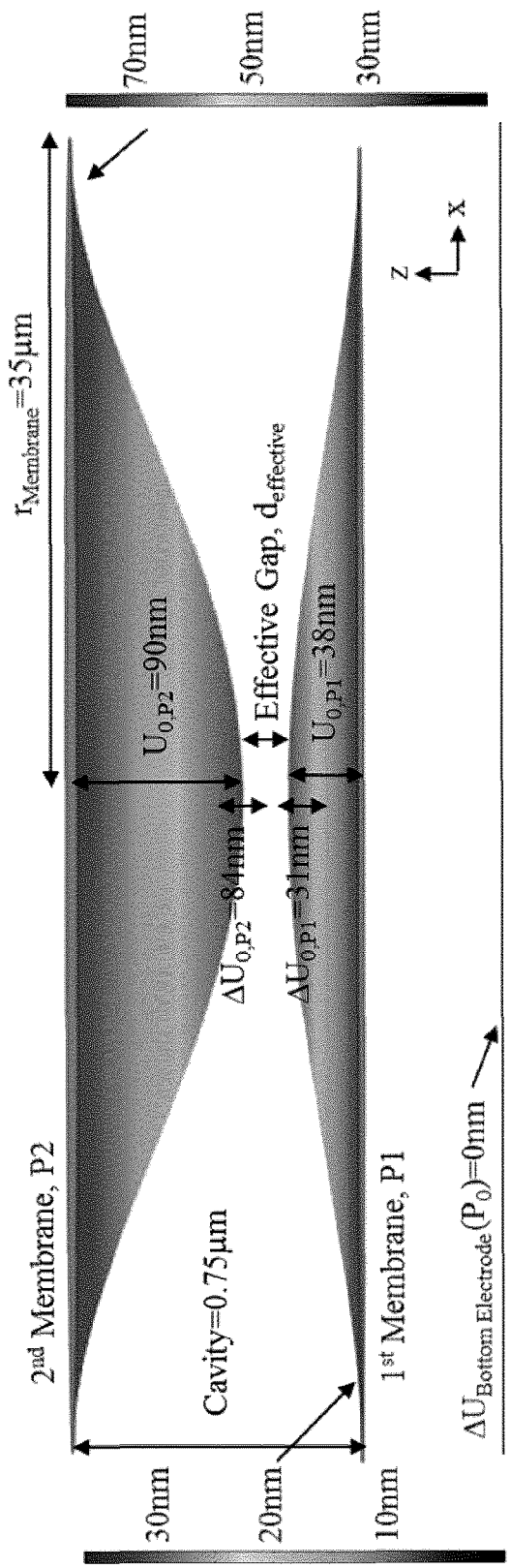
FIG. 5 is a chart of the membrane displacement of an example of the disclosed CMUTs in which there are two deflectable membranes.

FIG. 5 shows example simulation results for the example CMUT 100 of FIG. 3. In this example, the radius of each deflectable membrane 105 is about 35 μm, resulting in a resonant frequency of about 4 MHz, assuming the geometry dimensions listed in Table I and the common properties of the layers from COMSOL material library. In the simulation, the static membrane 110 and the middle deflectable membrane 105b were grounded, while the upper deflectable membrane 105a was driven by a DC bias voltage of about 135V.

FIG. 5 is an example membrane displacement map (showing the displacements U due to the DC bias voltage, and the vibrational amplitude ΔU due to the AC signal) of the membranes 105, 110 of the example CMUT 100, based on simulation results. $U_{0,P0}$ represents the displacement of the static membrane 110, $U_{0,P1}$ represents the displacement of the middle deflectable membrane 105b, and $U_{0,P2}$ represents the displacement of the top deflectable membrane 105a, where the displacements shown are the result of applying the bias voltage of about 135V. As shown in FIG. 5, the middle and upper deflectable membranes 105b, 105a (labeled in FIG. 5 as 1st membrane P1 and 2nd membrane P2, respectively) have an initial separation of about 0.75 μm (before application of any bias or electrical signal). At a bias voltage of about 135V (with an AC signal having amplitude of about 15V and frequency of about 4 MHz superimposed thereon), the static membrane 110 ($P_0$ in FIG. 5) exhibits no displacement; the middle deflectable membrane 105b is drawn away from the static membrane 110 by about 38 nm and exhibits a vibrational amplitude of about 31 nm; and the upper deflectable membrane 105a is drawn towards the static membrane 110 by about 90 nm and exhibits a vibrational amplitude of about 84 nm. Thus, at a DC bias voltage of about 135V and an AC signal of about 15V at about 4 MHz superimposed thereon, the effective gap $d_{effective}$ between the upper and middle deflectable membranes 105a, 105b is about 622 nm.

Figure 6:
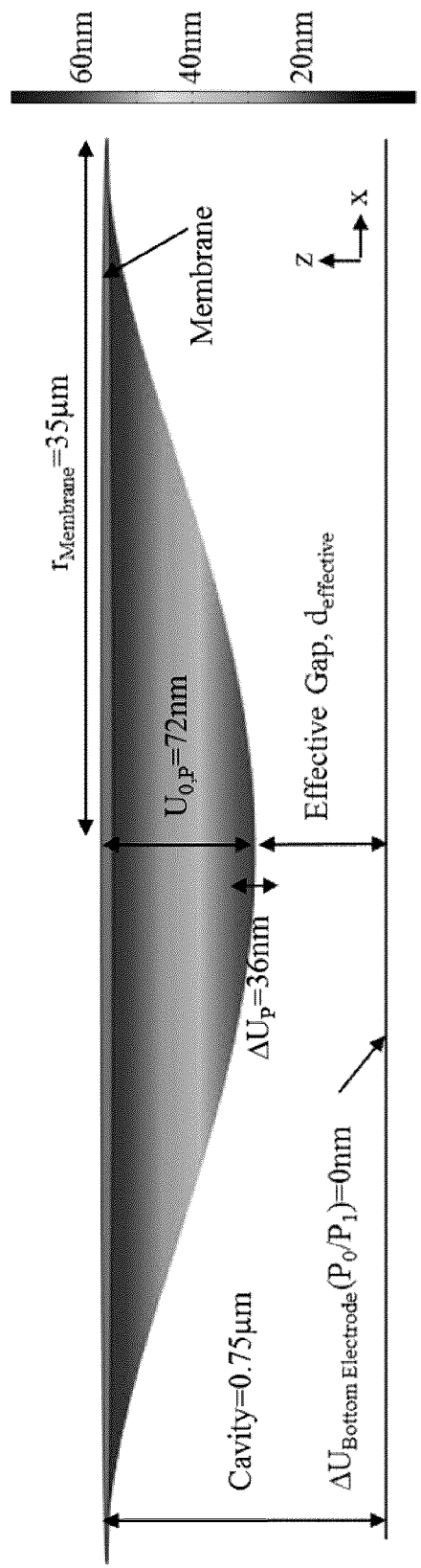
FIG. 6 is a chart of the membrane displacement of an example conventional CMUT.

FIG. 6 is an example membrane displacement map (showing the displacements U due to the DC bias voltage, and the vibrational amplitude ΔU due to the AC signal) of the single deflectable membrane 405 of a conventional CMUT 400, based on simulation results. The CMUT 400 in this example has a radius of about 35 μm, with a grounded bottom electrode 410 and an applied DC bias voltage of about 135V (with AC signal of about 15V at about 4 MHz superimposed thereon) on the deflectable membrane 405. $U_{0,P}$ represents the displacement of the single deflectable membrane 405. As shown in FIG. 6, the deflectable membrane 405 is initially about 0.75 μm away from the bottom electrode 410. At a bias voltage of about 135V and an AC signal of about 15V at about 4 MHz superimposed thereon, the deflectable membrane 405 is drawn towards the bottom electrode 410 by about 72 nm (resulting in an effective gap of about 678 nm) and exhibits a vibrational amplitude of about 36 nm.

The simulations show, as illustrated in FIG. 5, that in the example CMUT 100, the electrostatic force between the deflectable membranes 105a, 105b can pull the middle deflectable membrane 105b away from the static membrane 110 while the upper deflectable membrane 105a is being pulled towards the static membrane 110. An advantage of this configuration is that by allowing the middle deflectable membrane 105b to be free to move and to be pulled away from the static membrane 110, the effective gap $d_{effective}$ between the two deflectable membranes 105a, 105b may be reduced. Therefore, the sensitivity of the CMUT 100, which is proportional to the effective capacitance, may be enhanced. Furthermore, the effective gap $d_{effective}$ may be adjusted (e.g., by adjusting the bias voltage) as desired (e.g., where different applications require different sensitivity). This typically is not possible with conventional CMUTs 400, as the effective gap is dependent on the deflection of the single deflectable membrane 405 (since the bottom electrode 410 of the conventional CMUT 400 cannot deflect).

Comparison between the example simulations results for the disclosed example CMUT 100 (example results shown in FIG. 5) and the conventional CMUT 400 (example results shown in FIG. 6) shows that for the same DC bias voltage of about 135V, the upper deflectable membrane 105a of the disclosed CMUT 100 deflects more than the conventional CMUT membrane 405, in this instance $U_{P2}$=90 nm compared to $U_P$=72 nm. Therefore, the power generation capability of the disclosed CMUT 100 in transmitting mode may also be improved compared to a conventional CMUT 400.

In the example disclosed CMUT 100, the insulator 125 (e.g. comprising nitride) may not be required. In a conventional CMUT 400, the insulator 425 is typically deposited on the bottom electrode 410 to insulate the bottom electrode 410 and avoid shorting (which may occur in the conventional CMUT 400 when the single membrane 405 deflects to a large amount to unintentionally contact the bottom electrode 410). The omission of the insulator 125 from the example disclosed CMUT 100 may be possible because the displacement of the middle deflectable membrane 105b may be adjusted as necessary (e.g., by the application of appropriate bias voltage to the middle deflectable membrane 105b) to avoid unintentional contact with the upper deflectable membrane 105a. The omission of the insulator 125 may result in elimination of electric field drops over the insulator 125, which in return may help to improve the power consumption of the example disclosed CMUT 100 and lower the required driving voltage.

Figure 7:
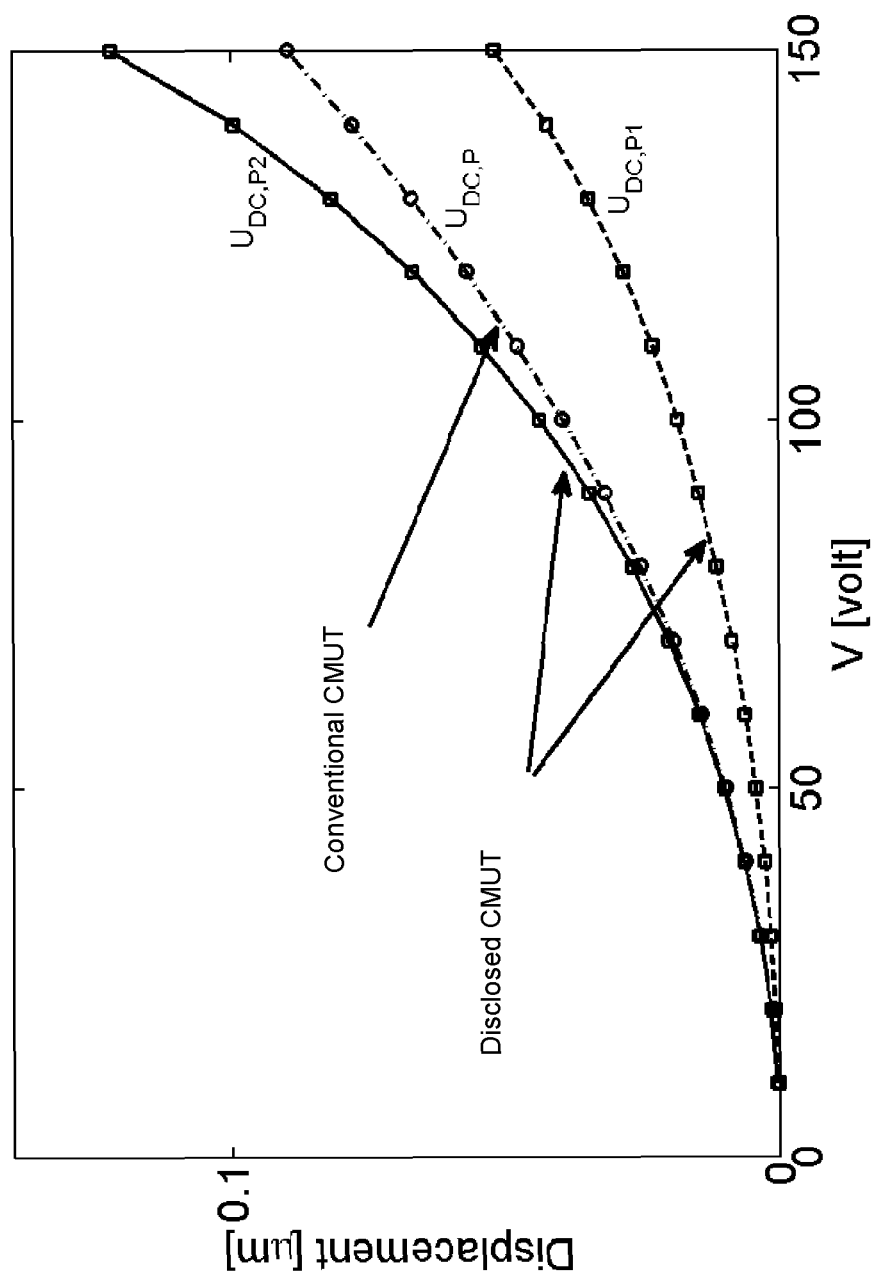
FIG. 7 is a chart comparing membrane displacement of an example of the disclosed CMUTs with that of an example conventional CMUT, for a range of biasing voltages.

Electromechanics voltage sweep simulations were also performed for an example of the disclosed CMUT 100 (as shown in FIG. 3) and a conventional CMUT 400 (as shown in FIG. 4) for a DC bias voltage ranging from about 10V to about 150V applied to the upper deflectable membranes. The static membrane 110 and the bottom electrode 410 were grounded in both cases, along with the middle deflectable membrane 105b in the disclosed CMUT 100. FIG. 7 presents the simulations results for the middle deflectable membrane 105b ($U_{DC,P1}$) and upper deflectable membrane 105a ($U_{DC,P2}$) of the example disclosed CMUT 100, as well as the single deflectable membrane 405 of the conventional CMUT 400 ($U_{DC,P}$). The example results indicate that by increasing the nominal pull down bias voltage, the displacement of the upper deflectable membrane 105a in the disclosed CMUT 100 exponentially diverged from the displacement of the single deflectable membrane 405 in the conventional CMUT 400. Therefore, in the example disclosed CMUT 100, greater displacement may be achieved for the same bias voltage compared to the conventional CMUT 400. Similarly, a smaller transducer pull down voltage may be used to attain a desired membrane displacement, hence improving power consumption and/or safety of the disclosed CMUT 100.

Electromechanics time-dependent simulations were also performed to compare the behavior of the example disclosed CMUT 100 to the conventional CMUT 400 when an AC term is superimposed on the DC bias voltage to force the deflectable membranes 105, 405 to vibrate, in order to generate acoustic power.

Figure 8:
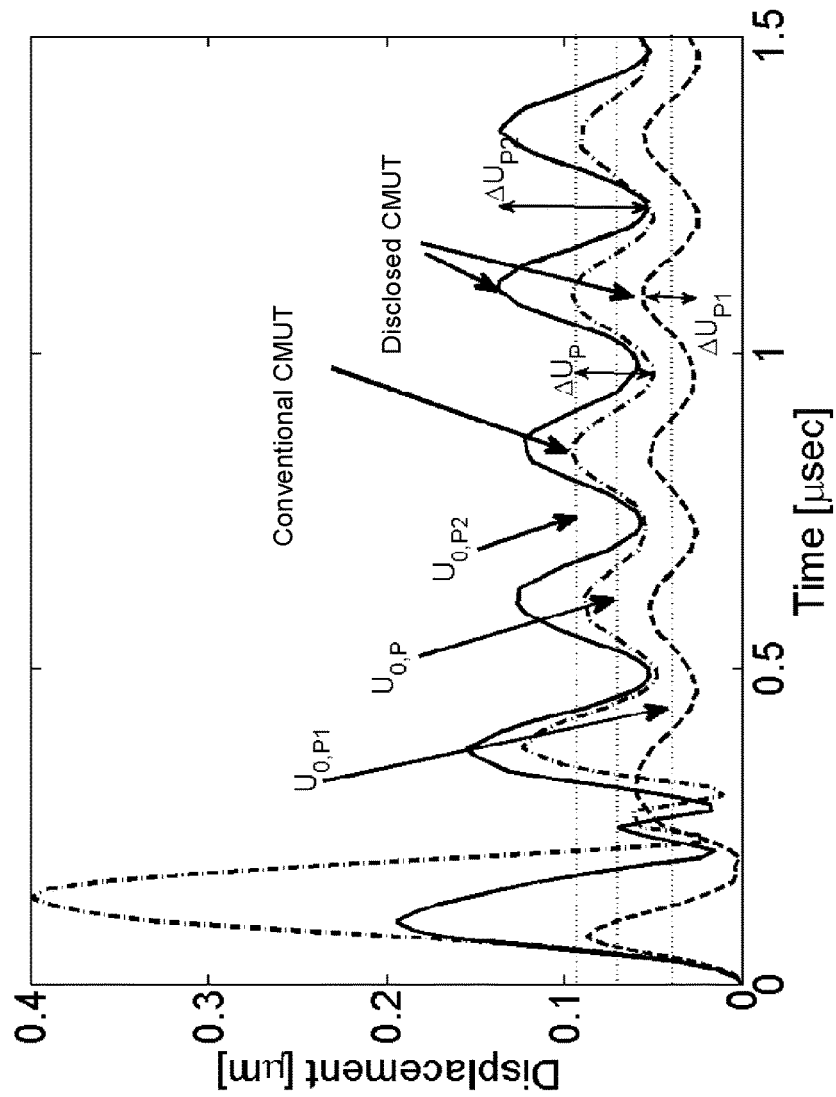
FIG. 8 is a chart comparing transient membrane displacement of an example of the disclosed CMUTs with that of an example conventional CMUT.

FIG. 8 presents example results for the example CMUT 100 of FIG. 3, fabricated as listed in Table I with a radius of about 35 μm, and compares it with example results for the conventional CMUT 400 of FIG. 4 having the same radius. From FIG. 8, it can be seen that for the same applied voltage (in this case, DC voltage of about 135V, AC signal of about 15V at a frequency of about 4 MHz superimposed thereon), the upper deflectable membrane 105a of the disclosed CMUT 100 vibrates with larger amplitude than the single deflectable membrane 405 of the conventional CMUT 400, as a greater membrane DC deflection ($U_0$) may enhance the deflectable membrane's vibration in response to an AC signal, thus increasing the power generation capability of the CMUT 100. The oscillation amplitude for a bias voltage about 135V with AC signal of about 15V at about 4 MHz superimposed thereon are illustrated in FIGS. 5 and 6, described above, and also presented in Table III below. Table III also lists the corresponding accelerations of the deflectable membranes 105, 405.

TABLE III

| | Layer | $U_0$ [nm] | $\Delta U$ [nm] | Acceleration [m/s$^2$] |
|---|---|---|---|---|
| Disclosed CMUT | Upper deflectable Membrane (P2) | 90 | 84 | $2.66 \times 10^7$ |
| | Middle deflectable Membrane (P1) | 38 | 31 | $9.8 \times 10^6$ |
| | Static Membrane (P0) | 0 | 0 | 0 |
| Conventional CMUT | Single deflectable Membrane (P) | 72 | 36 | $1.16 \times 10^7$ |
| | Bottom Electrode (P0) | 0 | 0 | 0 |

As the amplitude of membrane vibration and acceleration are proportional to the transducer generated power, the larger vibration of the example disclosed CMUT 100 compared to the conventional CMUT 400 may be expected to result in greater generated power.

Figure 9:
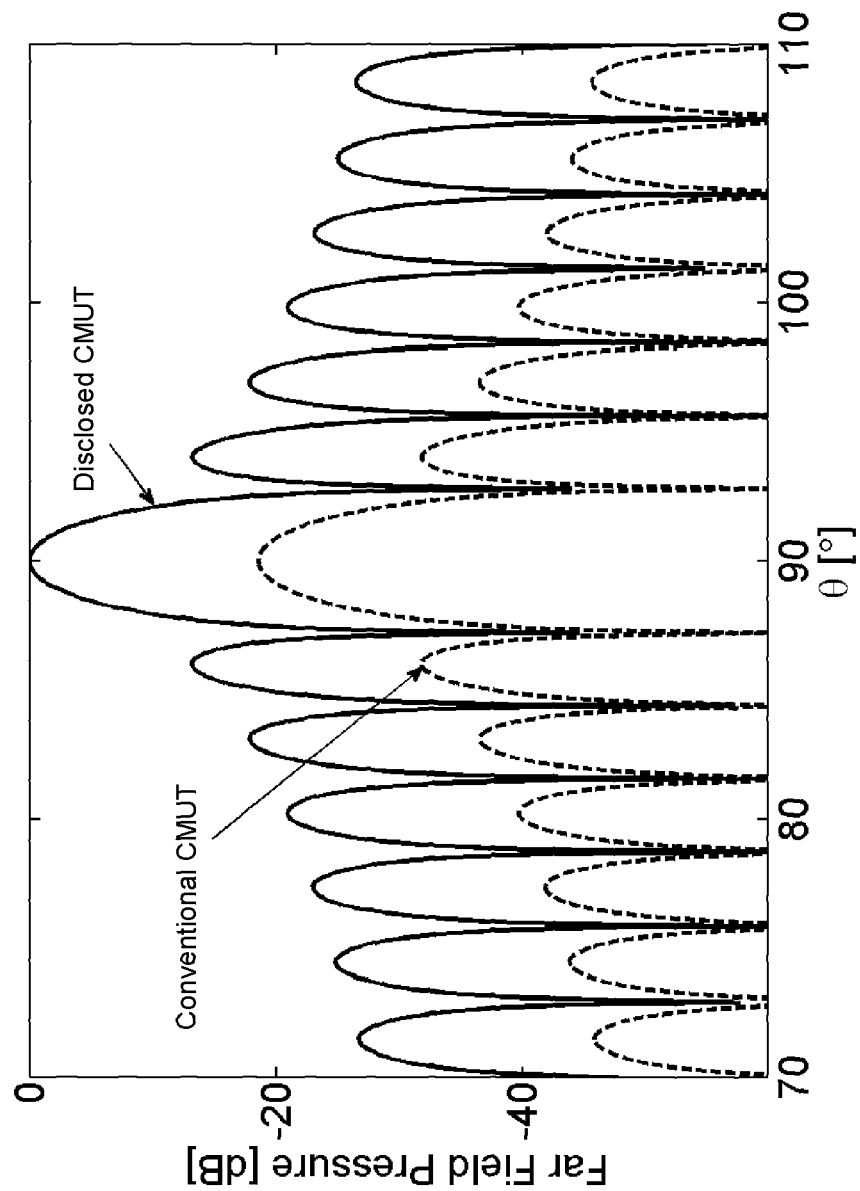
FIG. 9 is a chart comparing normalized beam shapes of an example array of the disclosed CMUTs with that of an example array of conventional CMUTs.

FIG. 9 shows the acoustic simulation results for arrays comprising the example disclosed CMUT 100 of FIG. 3 and comprising the conventional CMUT 400 of FIG. 4, operating in immersion mode (water) at a frequency of about 4 MHz. The presented results are from arrays with N=101 number of elements in a row, separated by a distance of about 5 μm edge to edge from each other. As shown in FIG. 9, far field pressure of the example disclosed CMUT 100 was found to be more than 20 dB higher than the conventional CMUT 400, when both are driven with the same DC and AC voltages.

Three or More Deflectable Membranes

In some examples, the disclosed CMUT may include more than two deflectable membranes. The inclusion of additional deflectable membranes may be useful for improving the sensitivity and/or power output of the CMUT. Each deflectable membrane may be made of the same or different material and/or dimensions, and may be driven by the same or different driving voltage, for example.

Figure 10:
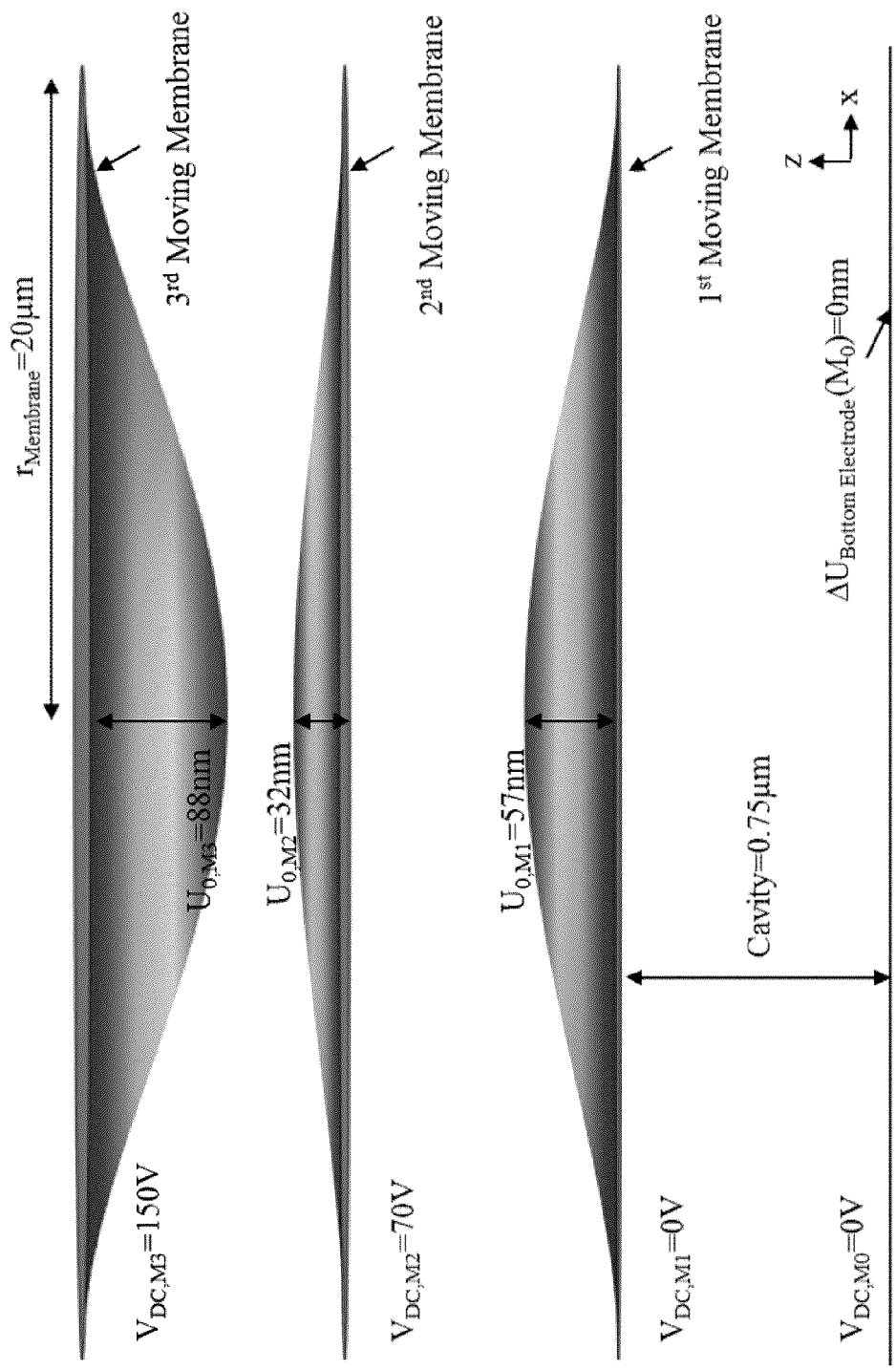
FIGS. 10 and 11 are charts of the membrane displacement of an example of the disclosed CMUTs in which there are three deflectable membranes, at different biasing voltages.
Figure 11:
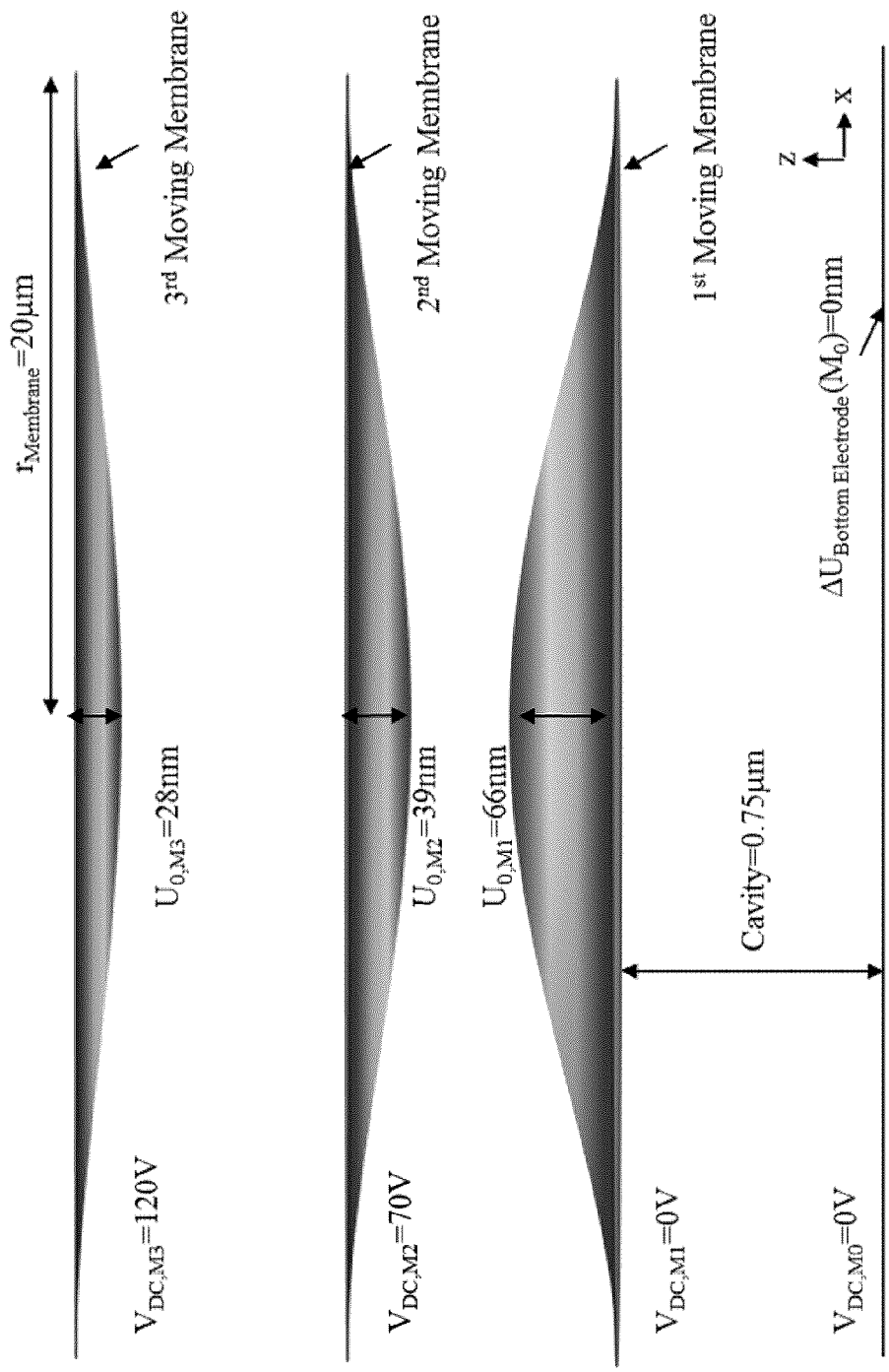

FIGS. 10 and 11 show displacement maps of an example of the disclosed CMUT, where the CMUT includes three deflectable membranes and a fixed bottom electrode. In this example the deflectable membranes may be made of a suitable material such as polysilicon, and may have dimensions such as a thickness of about 0.5 μm, a radius of 20 μm and be spaced from each other and the static membrane with a cavity height of about 0.75 μm.

In the simulation illustrated in FIG. 10, the upper-most deflectable membrane (M3) of the example three-membrane CMUT was driven with a DC bias voltage of about 150V, and the deflectable membrane immediately below it (M2) was biased with a DC bias voltage of about 70V. The remaining deflectable membrane (M1) and the static membrane (M0) were grounded. As shown in FIG. 10, at these biasing voltages, the upper-most deflectable membrane M3 was found to have a displacement $U_{0,M3}$ of about 88 nm towards the static membrane M0; the next deflectable membrane M2 was found to have a displacement $U_{0,M2}$ of about 32 nm away from the static membrane M0; and the remaining deflectable membrane M1 was found to have a displacement $U_{0,M1}$ of about 57 nm away from the static membrane M0.

In the simulation illustrated in FIG. 11, the upper-most deflectable membrane (M3) of the example three-membrane CMUT transducer was driven with a DC bias voltage of about 120V, while the other conditions remain the same as described above for FIG. 10. As shown in FIG. 11, at these biasing voltages, the upper-most deflectable membrane M3 was found to have a displacement $U_{0,M3}$ of about 28 nm towards the static membrane M0; the next deflectable membrane M2 was found to have a displacement $U_{0,M2}$ of about 39 nm towards the static membrane M0; and the remaining deflectable membrane M1 was found to have a displacement $U_{0,M1}$ of about 66 nm away from the static membrane M0.

Note that the displacements shown in FIGS. 10 and 11 are not to scale.

Thus, these simulations illustrate that each deflectable membrane may be displaced towards or away from its neighbor(s) by simply varying the voltage difference between the two neighboring membranes (e.g., M2 and M3) and/or by changing the polarity of the bias voltages. Since the effective gap between membranes affect the sensitivity of the CMUT, the ability to adjust the effective gap through adjusting the biasing voltage may allow the same CMUT to be used in applications requiring different sensitivities and/or power generation. This may broaden the operating range and/or functionality of the disclosed CMUT, such as where different transducer sensitivities or maximum standing pressures are required for different applications. The same working principle may be applied to other variations of the disclosed CMUT with any number of deflectable membranes.

FURTHER EXAMPLE STUDIES

Example studies were carried out on various examples of the disclosed CMUT. Discussions of these are provided below for the purpose of illustration only. These examples are not intended to be limiting.

Example 1

Figure 12:
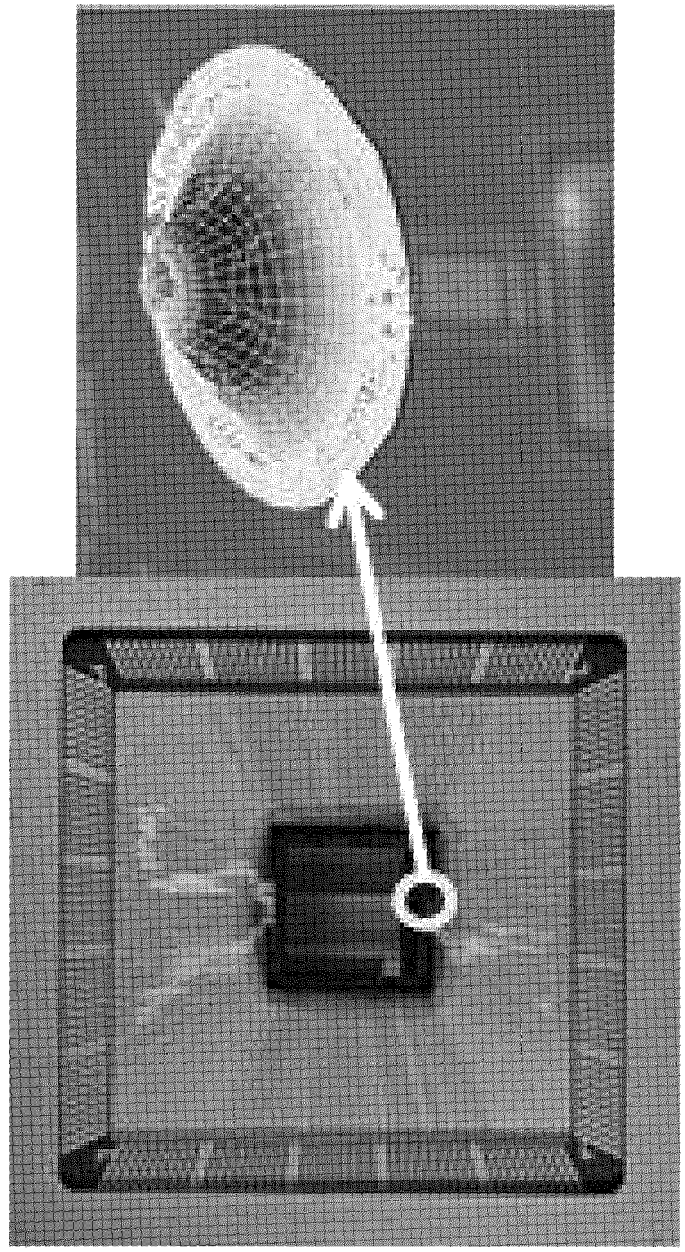
FIG. 12 shows an enlarged photograph and an optical image of an example of the disclosed CMUTs, fabricated using a PolyMUMPs™ technique.

A set of seven example single-cell disclosed CMUT devices and a set of five example single-cell conventional CMUT devices were fabricated employing an example of the PolyMUMPs fabrication technique, for example as described above. These transducers were designed based on simulation results (e.g., as described above), and with radii of 30, 35, 40, 42, 45, 50 and 55 μm for the disclosed CMUTs, and 30, 35, 40, 45 and 55 μm for the conventional CMUTs. An enlarged image of the fabricated chip for an example disclosed CMUT is shown on the left side of FIG. 12. The chip dimensions in this example are about 4.75 mm by 4.75 mm. An optical image of the 55 μm radius example of the disclosed CMUT is illustrated on the right side of FIG. 12, along with the measured first mode deflection profile at 9 V DC bias superimposed by a 1 V AC signal and at a frequency of 1.48 MHz.

Figure 13:
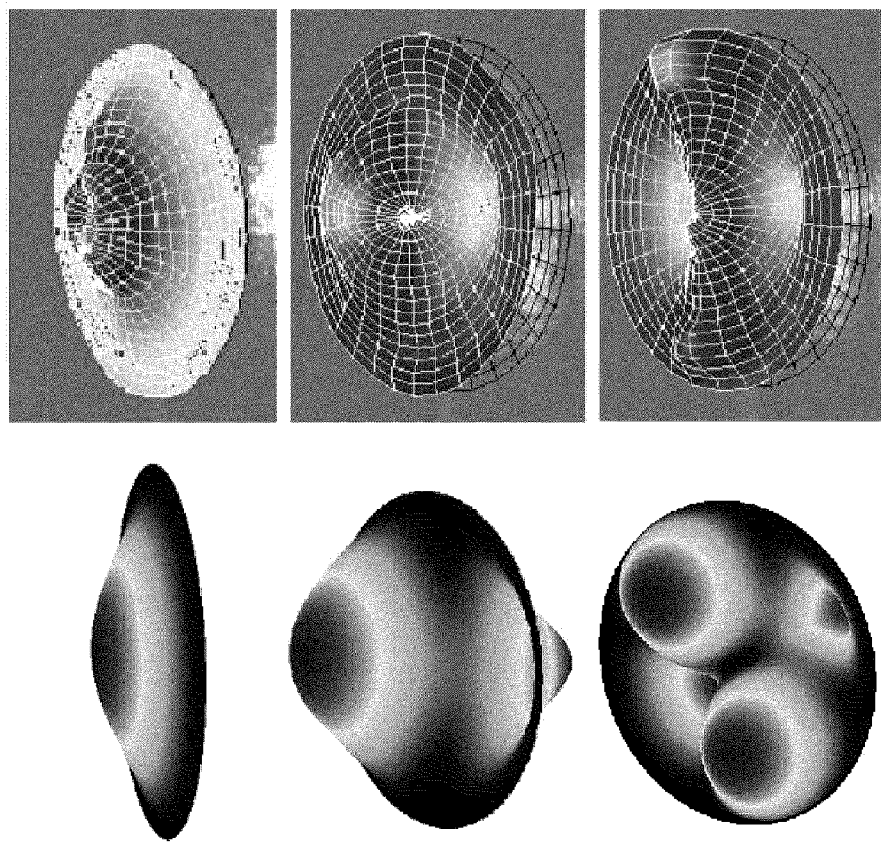
FIG. 13 shows simulated and measured deflection profiles of an example of the disclosed CMUTs at first, second and fourth natural resonant frequencies.

Three dimensional (3D) COMSOL simulations were conducted to investigate the deflection profile of examples of the disclosed CMUTs at their higher natural resonant frequency modes. The simulation results for the first (top), second (middle), and forth (bottom) natural frequencies (modes) of a 40 μm radius example of the disclosed CMUT are illustrated on the left side of FIG. 13. The simulated profiles were found to be similar to conventional CMUTs profiles investigated in this example study.

In order to validate the simulation results, examples of the disclosed CMUT devices were tested using a laser vibrometer Polytec Micro System Analyzer, MSA-500 (Polytec Inc., CA, USA). The devices were characterized with 9 V DC bias and an AC signal of 1 V which was limited by the vibrometer power supply. The deflection profiles of the 40 µm radius example disclosed CMUT, for the first (top), second (middle), and fourth (bottom) natural frequencies, are presented on the right side of FIG. 12. Comparing the images on the left and right sides of FIG. 12, the measured membrane vibration profiles were found to match the 3D COMSOL electromechanics simulation. Similar modes and comparisons were observed for the other example disclosed CMUT devices. The measured and simulated natural frequencies for the 40 µm radius example CMUT devices were found to be about 3.4 MHz and 3.7 MHz (1' mode), 6.3 MHz and 5.0 MHz ($2^{nd}$ mode) and 11.1 MHz and 10.3 MHz ($4^{th}$ mode), respectively. The slight differences between the measured and simulated values may be attributed to the geometry simplification for the simulations.

The Polytec Micro System Analyzer was used to measure the frequency response of the 40 µm radius example disclosed CMUT and a conventional CMUT over a frequency range from 0-15 MHz (step=3.1 kHz). The transducers were biased at 9 V DC superimposed with 1 V AC. Both of the transducers' frequency response profiles showed five resonant modes within the investigated frequency range. The transducers' first natural resonant frequencies were observed to be relatively close to each other, about 3.4 MHz for the example disclosed CMUT device and about 2.8 MHz for the conventional CMUT device.

Figure 14:
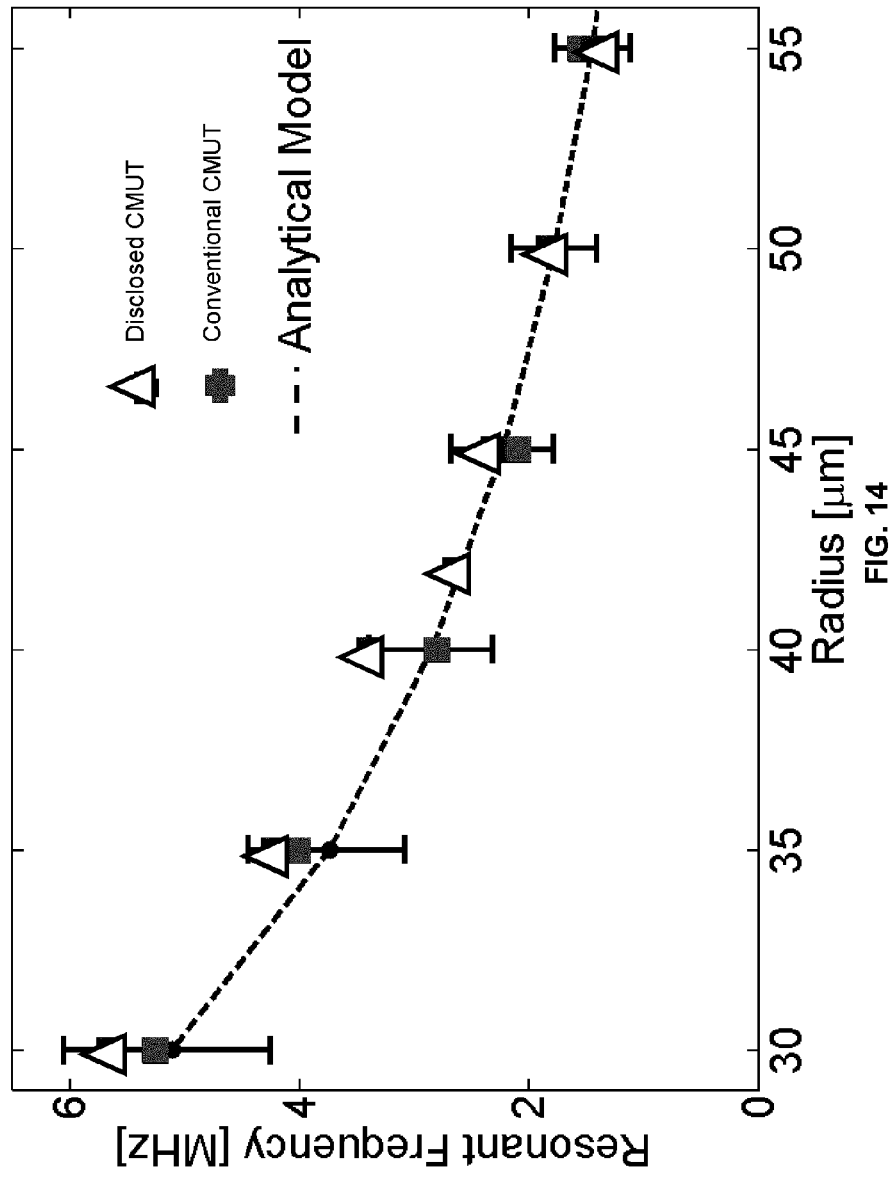
FIG. 14 is a chart comparing the natural resonant frequencies of examples of the disclosed CMUTs with that of conventional CMUTs.

An Agilent Precision Impedance Analyzer 4294A was used to measure the transducers' resonant frequencies at higher DC voltages, 40 V maximum, which was limited by the impedance analyzer power supply. Impedance measurements were performed and resonant frequencies of each device were extracted from the peaks in the measured impedance. The results were compared with an analytical model. The measured resonant frequencies at 30 V DC, superimposed with a 50 mV AC signal are presented in FIG. 14 for the example disclosed CMUTs and conventional CMUTs, along with the analytical model. Error bars in the analytical model may represent the uncertainty in the material properties used in the PolyMUMPs® fabrication process, described above. The model in this example assumed an initially flat membrane and did not include any curvature of the layers associated with the fabrication process and layer anchoring to the substrate (e.g., as in FIG. 21A). From FIG. 14, it can be seen that the results for both the examples of the disclosed CMUTs and conventional CMUTs were in reasonably good agreement with the analytical model for the same membrane radius.

The Polytec Micro System Analyzer was employed to measure the resonant frequencies of all the fabricated transducers at 10 V DC and the measurements were compared with Impedance Analyzer results. All the values were found to be in reasonably good agreement and within ±1% of each other.

Figure 15A:
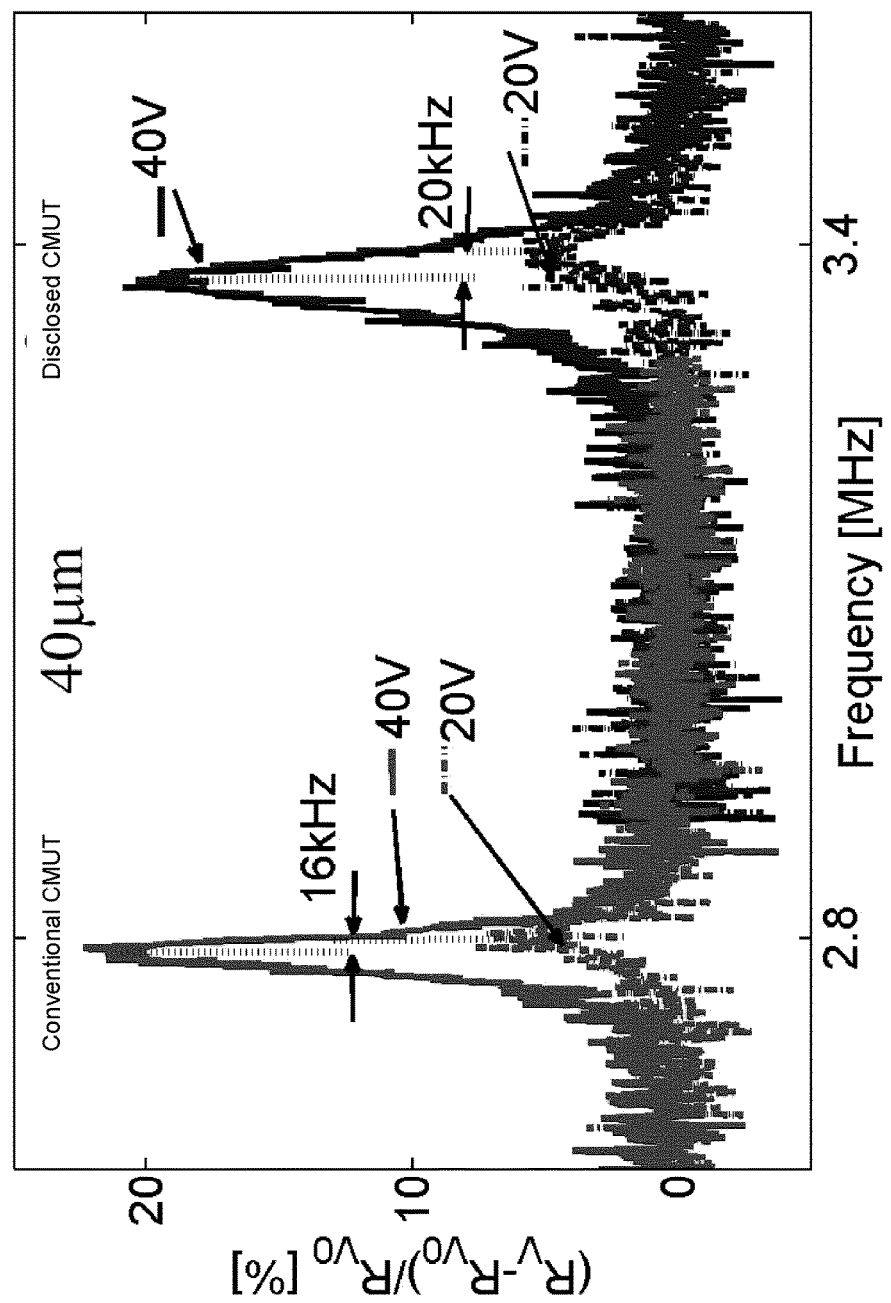
FIGS. 15A and 15B are charts comparing the normalized real part of the impedance for an example of the disclosed CMUTs with that of a conventional CMUT, at membrane radii of 40 μm and 55 μm.
Figure 15B:
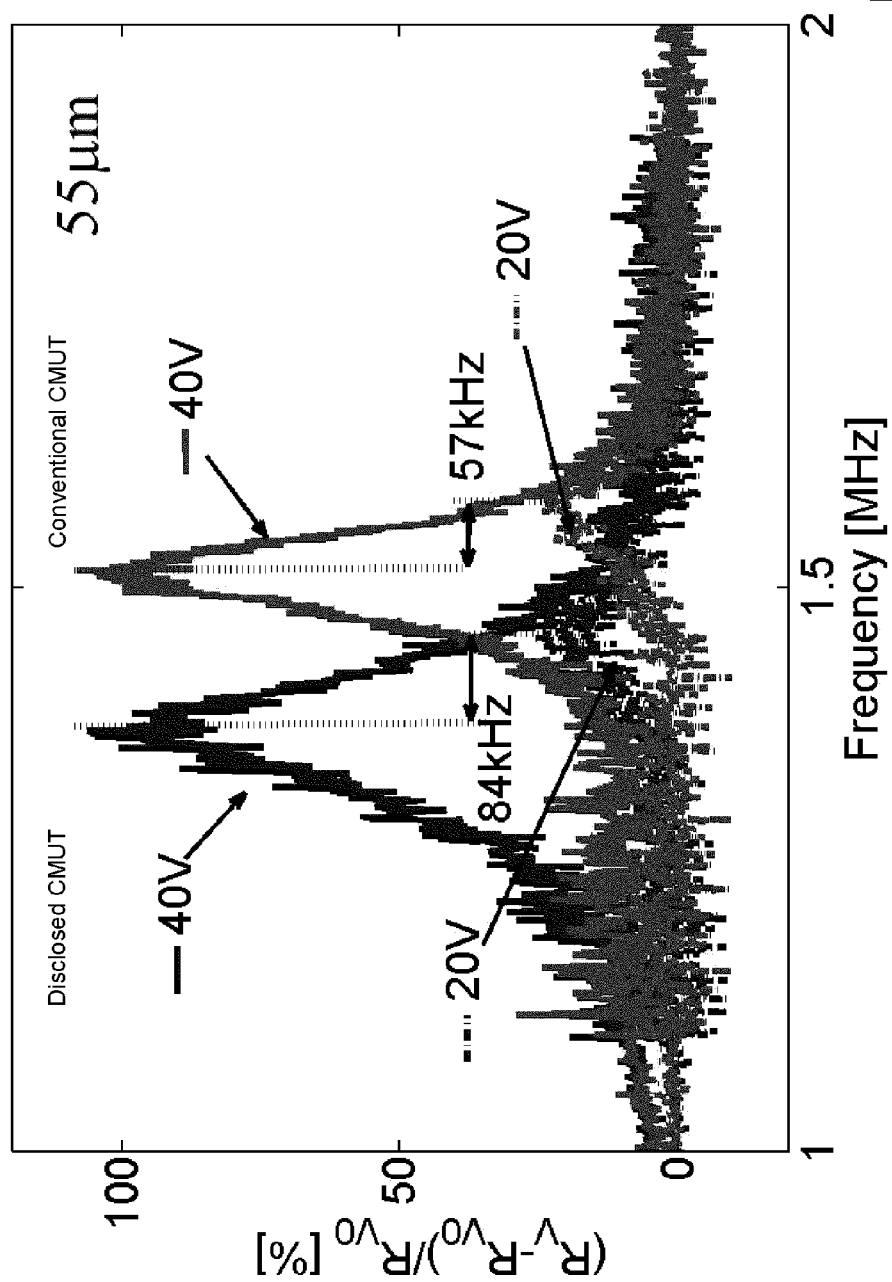

The normalized real part of the impedance for the 40 µm and 55 µm radius examples of the disclosed CMUT and conventional CMUT are illustrated in FIGS. 15A and 15B, respectively. The results are presented for a bias of 40 V DC (solid lines) and 20 V (dashed lines), both with a superimposed, 50 mV AC signal. From FIGS. 15A and 15B, it was observed that the resonant frequencies decreased when the DC bias voltage increased. This is likely due to the spring softening effect. By employing equations (1) and (2) below, this change in the resonant frequency may be interpreted as the change in the membrane spring constant k.

$$k = \frac{16\pi E_{membrane} t_{membrane}^3}{3(1-\upsilon^2)r_{membrane}^2} - \frac{\varepsilon_0 A_{membrane} V^2}{h_{effective}^3} + 4\pi\sigma t_{membrane} \quad (1)$$

$$\omega_r 2\pi f_r = \sqrt{\frac{k}{m_{membrane}}} \quad (2)$$

Assuming the same material and fabrication process, this frequency shift, $\Delta f_r$, may be represented by the second term in (1) for a given device, dimension, and voltage change, V. Therefore, a larger reduction in the device resonant frequency at a given V may be attributed to a smaller effective cavity height.

Figure 16A:
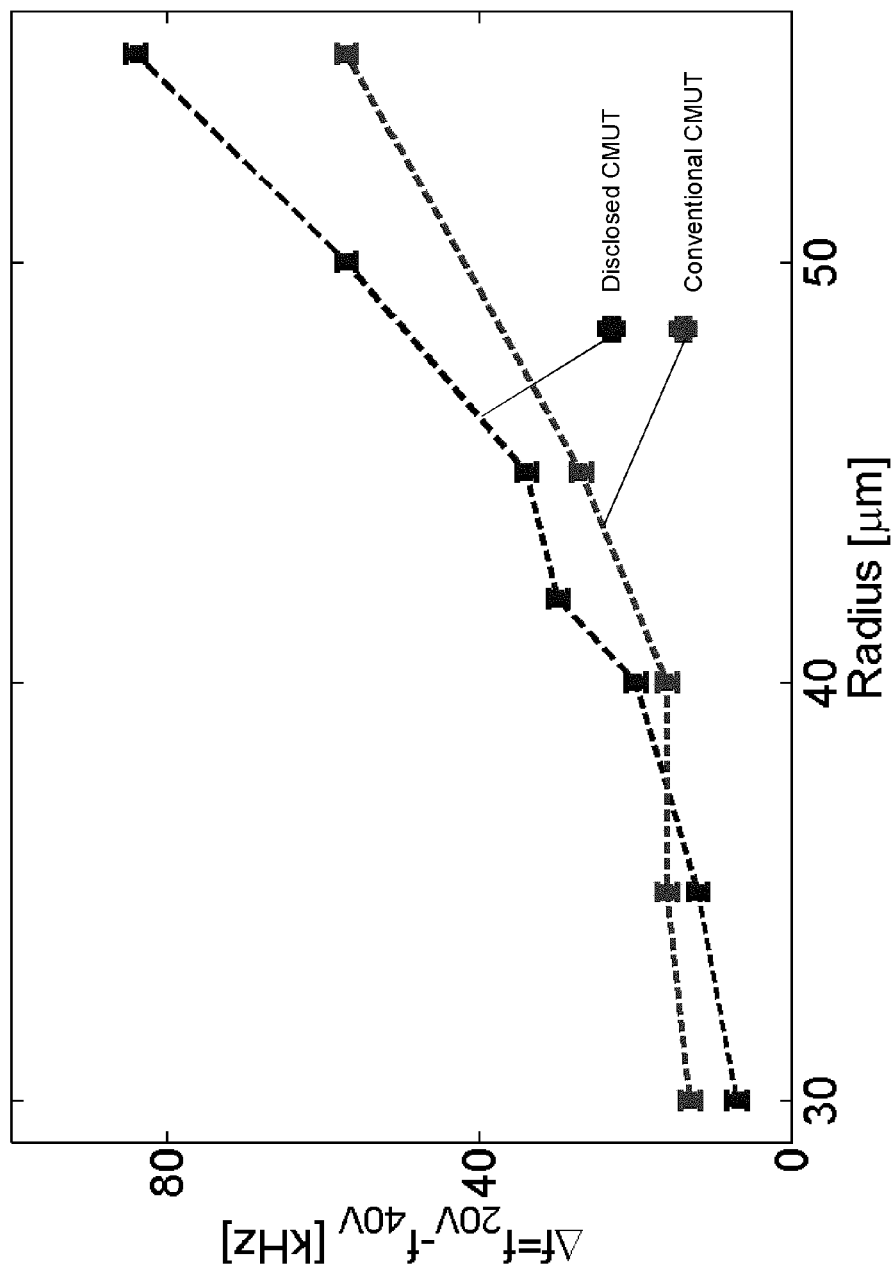
FIGS. 16A and 16B are charts showing a shift in the first natural resonant frequency peaks which may be due to the spring softening effect, and a shift in the derived spring constant comparing examples of the disclosed CMUTs with conventional CMUTs.
Figure 16B:
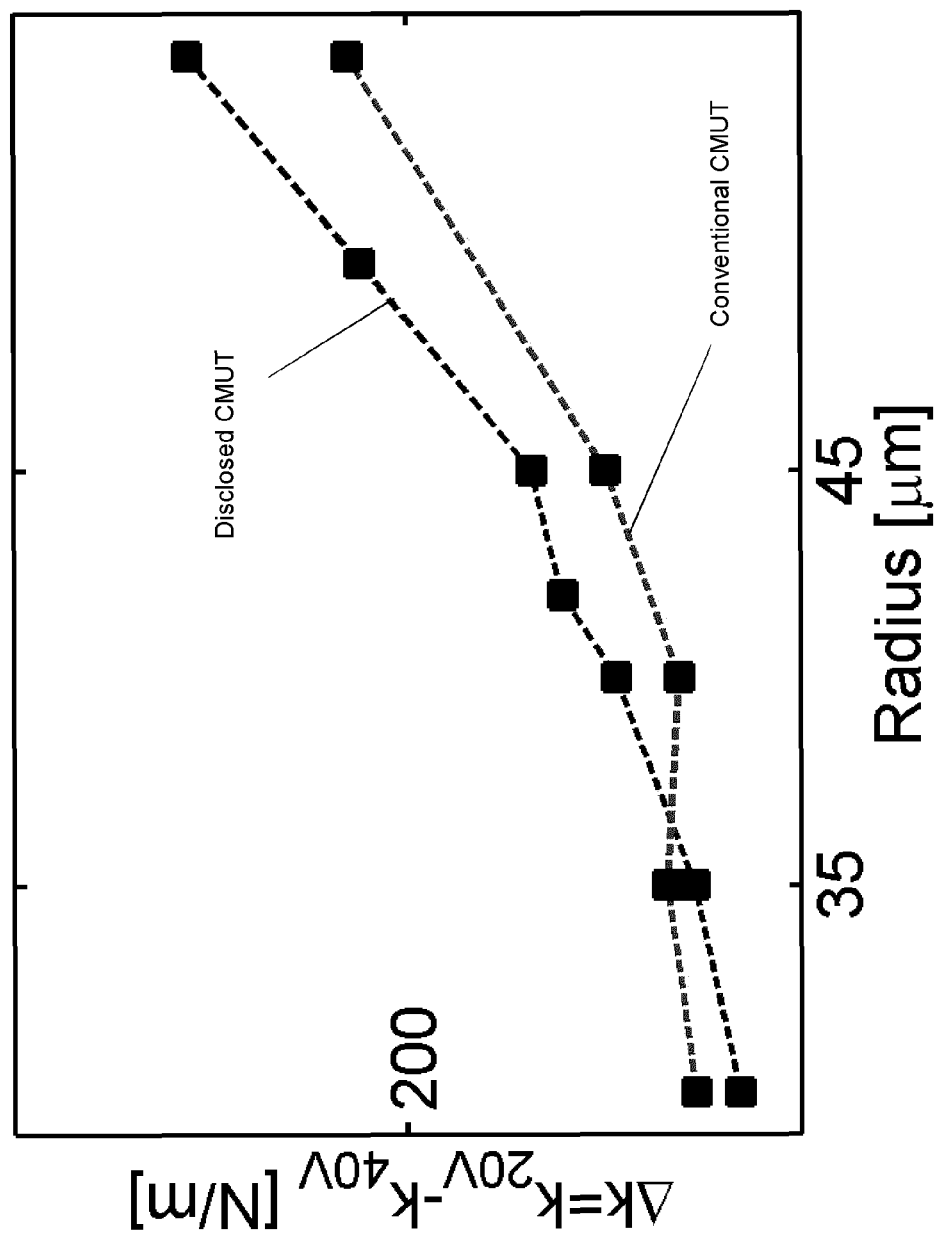

The measured reduction in the resonant frequencies (possibly due to the spring softening effect) of the example disclosed CMUTs and conventional CMUTs are illustrated in FIG. 16A, for a DC bias change from 20 V to 40 V. The equivalent change of the spring constant versus device dimensions is shown in FIG. 16B where it can be seen that the example disclosed CMUT devices were found to experience a larger resonant frequency shift for devices with radius above 35 µm. The shift also diverged from the conventional CMUT frequency shift for larger radii. Therefore, the effective cavity heights for the example disclosed CMUT devices may be smaller than the conventional CMUT cavity height at a given voltage. This may help to verify the discussions above, and may also confirm that the effective cavity height of the disclosed CMUT may be further reduced by the summation of both top and lower membranes deflections. The opposite phenomena for very small devices (e.g., 30 µm radius) may be due to the devices operating well below their nominal operating voltage (about >100 V calculated from the analytical model).

From this example study, it was found that device deflection profiles for fabricated examples of the disclosed CMUT, at different resonant frequency modes, were in good agreement with simulation results. It was also found that in the disclosed CMUT configuration, the generated electrostatic force due to the applied bias caused a downward deflection of the top membrane and an upward motion of the lower membrane. Therefore, the transducer effective gap may be less than that for conventional CMUTs.

The higher measured resonant frequency shifts found for a given device dimension and voltage may indicate a larger spring softening effect in the example disclosed CMUTs compared to conventional CMUTs, confirming a smaller effective cavity height in the example disclosed CMUTs. The reduction in the cavity height of the disclosed CMUT may help to enhance the transducer operational properties, such as sensitivity and/or power generation capability.

For the same DC bias, the deflection of the top membrane was found to be greater in the example disclosed CMUTs than that of conventional CMUTs with the same dimensions. It has been shown that in the example disclosed CMUTs, the required driving voltage has also been reduced compared to conventional CMUTs and created an increased membrane deflection for a given voltage, which may help to enhance the device acoustic output properties.

In the disclosed CMUTs, the lower membrane may be also deflectable and therefore the top membrane, where the contact is made, may be grounded while still preserving vibrational properties. This "reverse biasing" may be beneficial in health related applications, where the top membrane, which might come in contact with a patient's body, can be grounded instead of being biased at high voltages, thus offering greater patient safety. The sensitivity of the disclosed CMUTs may be also enhanced compared to conventional CMUTs, as the effective gap between two adjacent membranes may be reduced, which may be useful for imaging complex geometries where the reflected acoustic wave is often weak.

Example 2

In this example, examples of the disclosed CMUT and conventional CMUTs were fabricated employing a MEMSCAP sacrificial technique, PolyMUMPs®. In Table I the physical material properties used for this example study, which were selected to suit the fabrication process, are listed. The LPCVD deposited polysilicon in this technique had a minimal residual stress of 10 MPa, and may be considered small enough to not be included in the model. The Polysilicon Young's Modulus, Poisson's ratio and density were 158 GPa, 0.22, and 2328 g/cm$^3$, respectively. An image of the fabricated chip (about 4.75 mm×4.75 mm in size) is seen on the left side of FIG. 12. An optical image of the example disclosed CMUT is shown on the right side of FIG. 12. In the conventional CMUT, the P2 layer listed in Table I was used as the membrane, and a stack of the P1 and P0 layers of Table I was used as the fixed bottom electrode. For the examples of the disclosed CMUT devices, the top deflectable membrane was the P2 layer. Unlike the conventional CMUT, the P1 layer was used as the middle deflectable membrane. The P1 layer was suspended over the P0, which served as the static membrane. In both transducers, the cavity height between the top membrane and lower membrane/bottom electrode was defined by the sacrificial layer. The membrane radius for both devices was 65 µm.

In both the example disclosed CMUT and conventional CMUT devices, the top membrane, P2, was driven with a DC bias and both P1 and P0 layers were grounded. A DC voltage sweep measurements were used to investigate the catastrophic collapse voltage of the two transducers. It was found that the example disclosed CMUT and conventional CMUT devices exhibited non-reversible collapse behavior at 28±1 V and 33±1 V, respectively.

Figure 17:
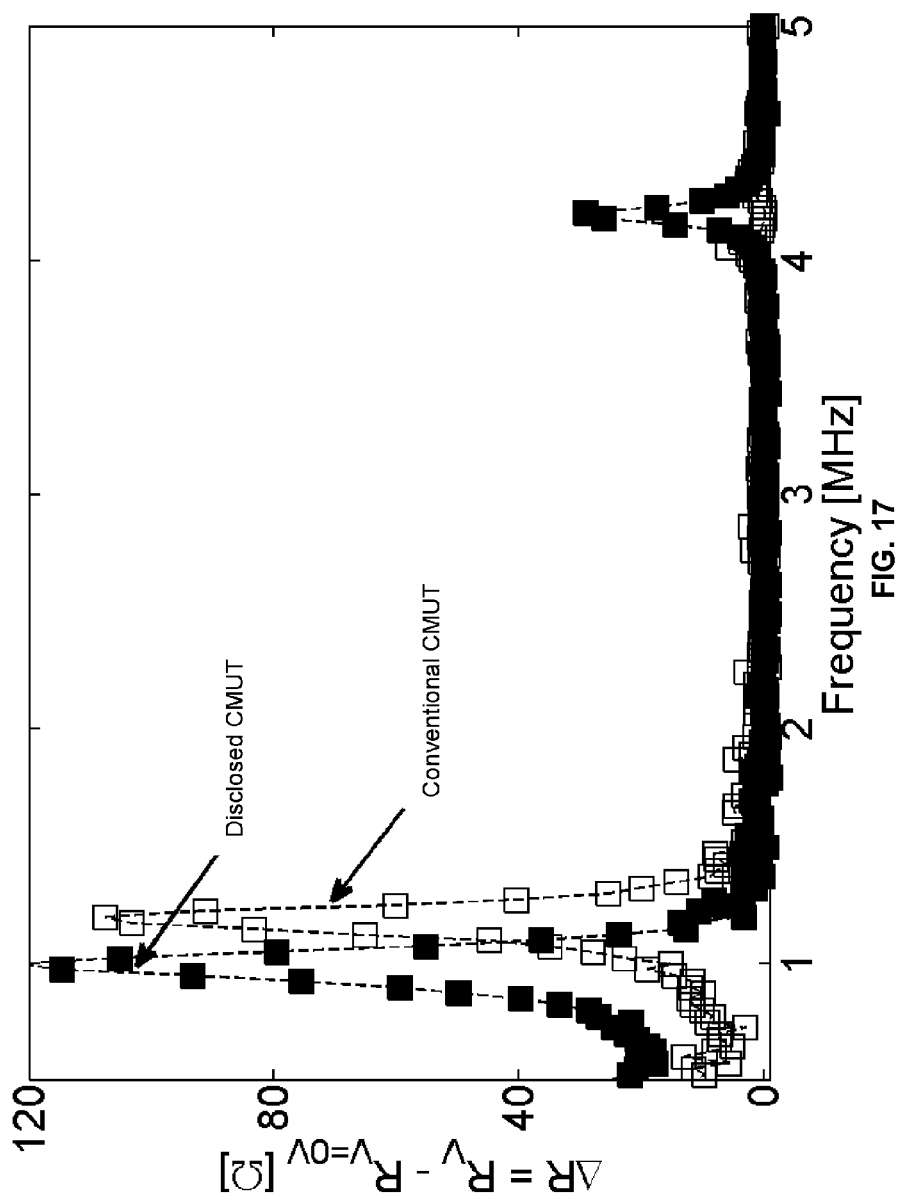
FIGS. 17, 18A and 18B are charts comparing the relative real part of the impedance of an example of the disclosed CMUTs with that of a conventional CMUT.

An Agilent Precision Impedance Analyzer 4294A was used to measure the transducers' mechanical resonant frequencies in air. In FIG. 17, the real part of the example disclosed CMUT's and conventional CMUT's impedances are shown. The example disclosed CMUT and conventional CMUT devices were driven at a pull down voltage of 25 V and 30 V, respectively; close to their respective collapse voltages. A small AC signal of 50 mV was superimposed on the device DC bias voltage to enable the impedance measurements.

From FIG. 17, the first mode resonant frequency of the example disclosed CMUT and conventional CMUT devices were found to be 1.0 and 1.2 MHz, respectively, within a 5 kHz accuracy. Simulations and calculations yielded resonant frequencies for these devices of 1.06 MHz, which was in reasonably good agreement with the measured data. The resonant frequencies of these transducers were also confirmed by a physical optical detection method, using a Polytec Micro System Analyzer MSA-500 Vibrometer, with 3 kHz accuracy. The vibrometer results were found to be in reasonably good agreement with the impedance measurements.

From FIG. 17, it can be seen that although the conventional CMUT was driven with a higher DC voltage, the example disclosed CMUT still showed a noticeably higher change in the transducer impedance and therefore membrane deflection. This, in turn, can be translated to a higher generated acoustic power.

Figure 18A:
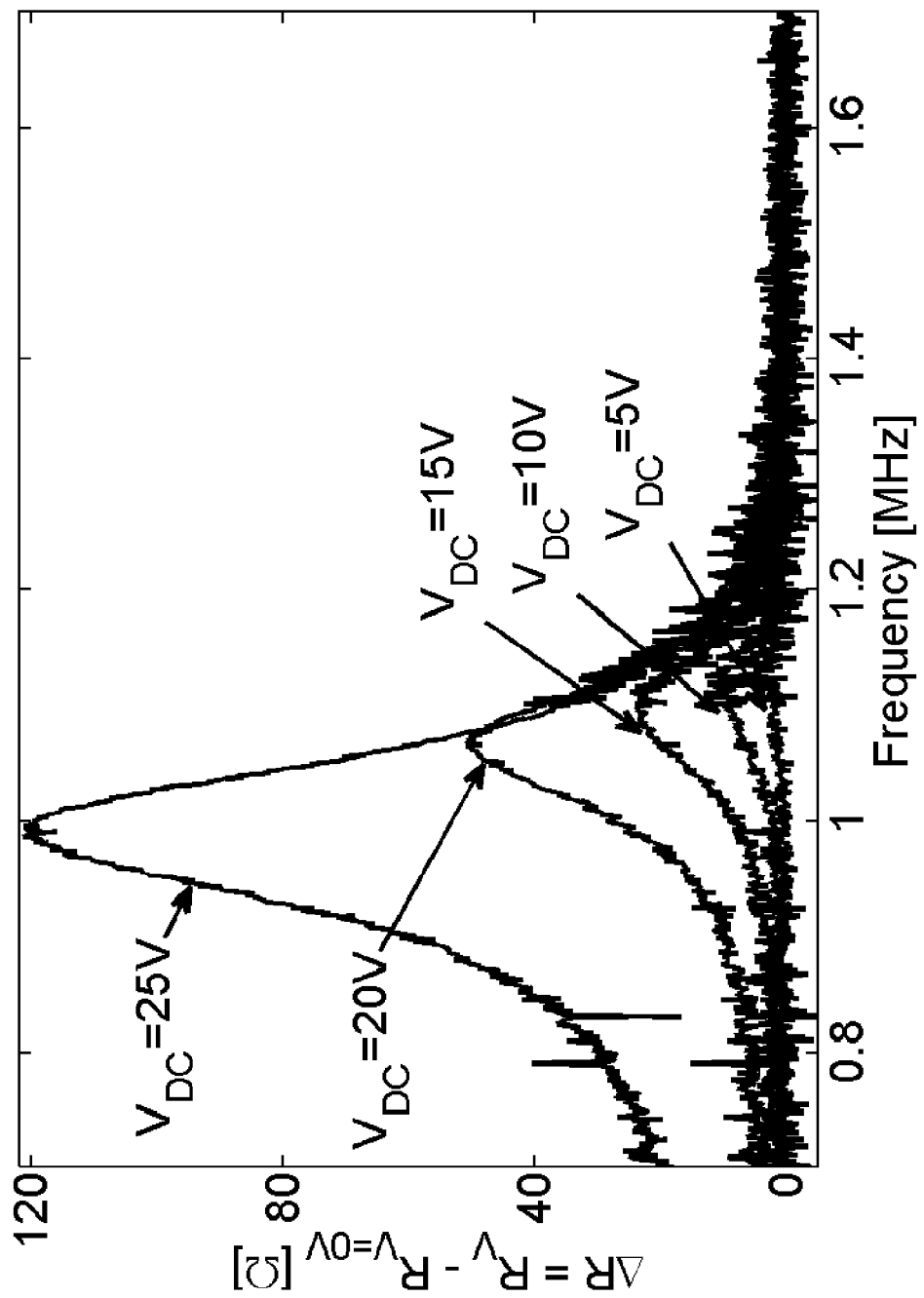
Figure 18B:
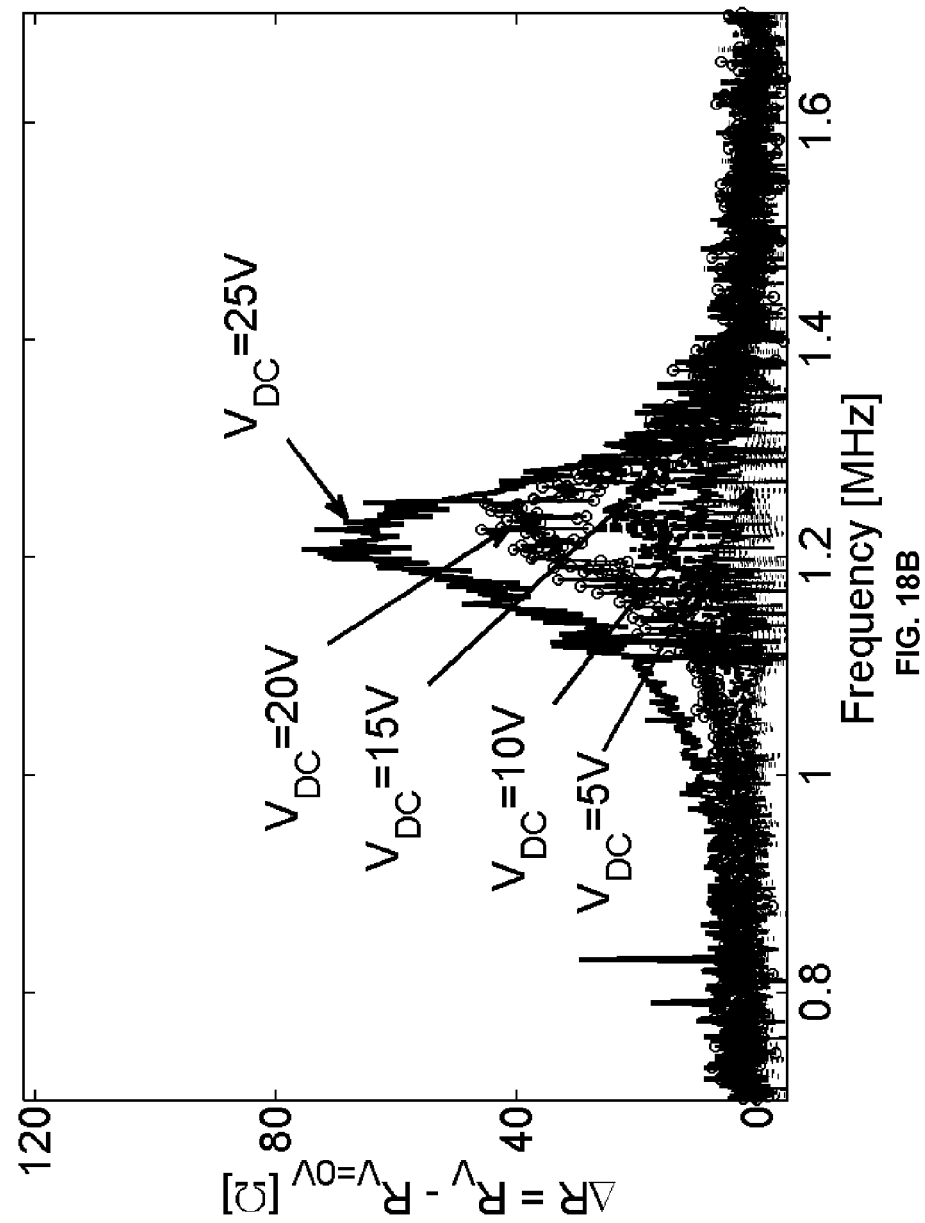

The DC voltage dependent real part of the impedances of the example disclosed CMUT and conventional CMUT transducers are shown in FIGS. 18A and 18B, respectively. The DC bias voltage was varied from 0-25 V.

From FIGS. 18A and 18B, it can be seen that the amplitude of the impedance was greater for the example disclosed CMUT for all bias voltages. The shift in the transducers' resonant frequencies observed for both the disclosed and conventional CMUT devices may be due to the spring softening effect, as discussed above.

A larger resonant frequency shift may be proportional to the change in the device effective cavity height. Comparing FIGS. 18A and 18B, it can be seen that the shift was larger for the example disclosed CMUT device, where at 25 V resonant frequency shift is 150 kHz, about 3 times that of the conventional CMUT. This may indicate that the example disclosed CMUT had smaller effective cavity height than the conventional CMUT, which may be the result of deflection of both of the two deflectable membranes in the example disclosed CMUT.

Figure 19A:
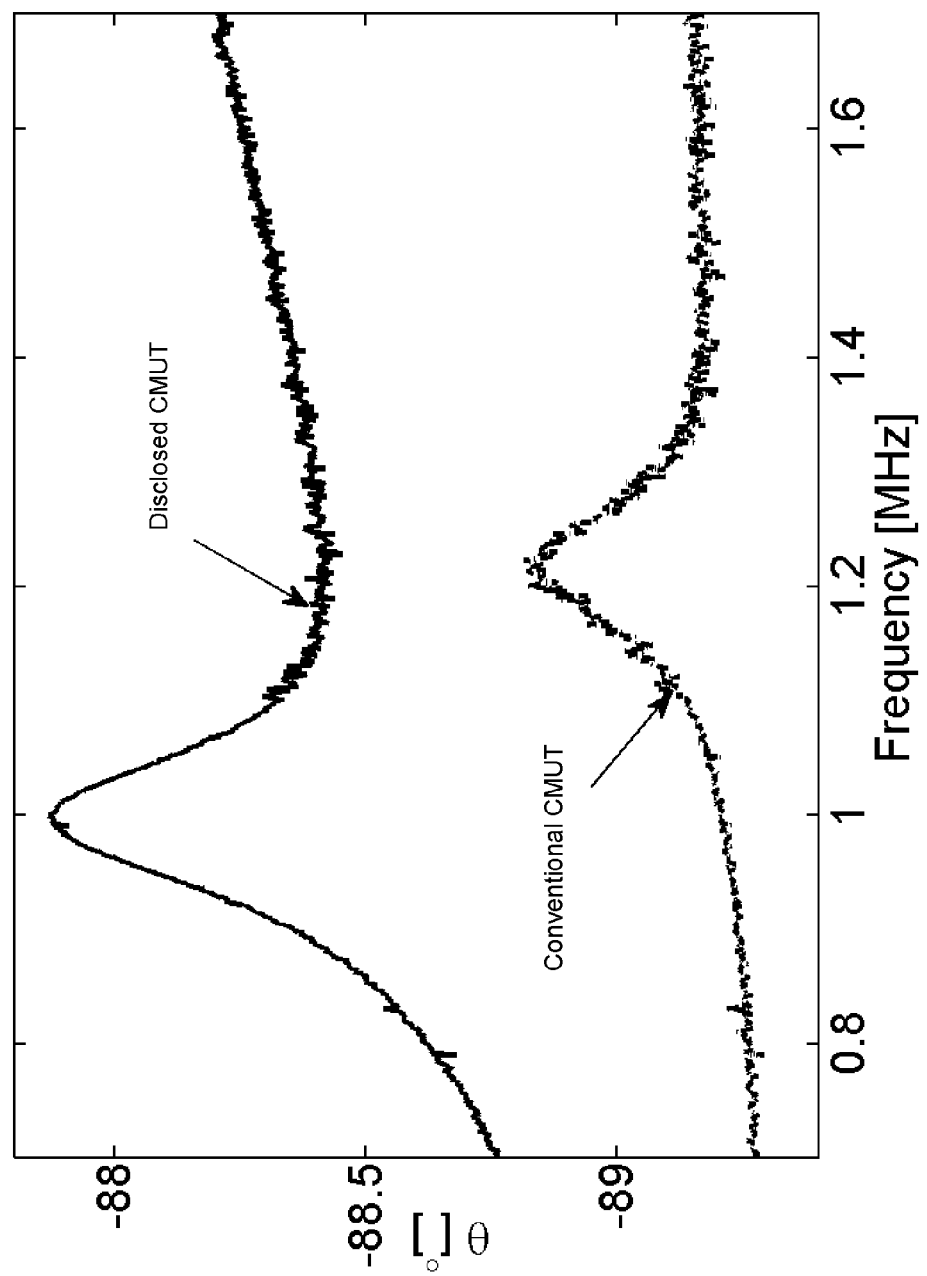
FIG. 19A is a chart comparing the phase change of an example of the disclosed CMUTs with that of a conventional CMUT.
Figure 19B:
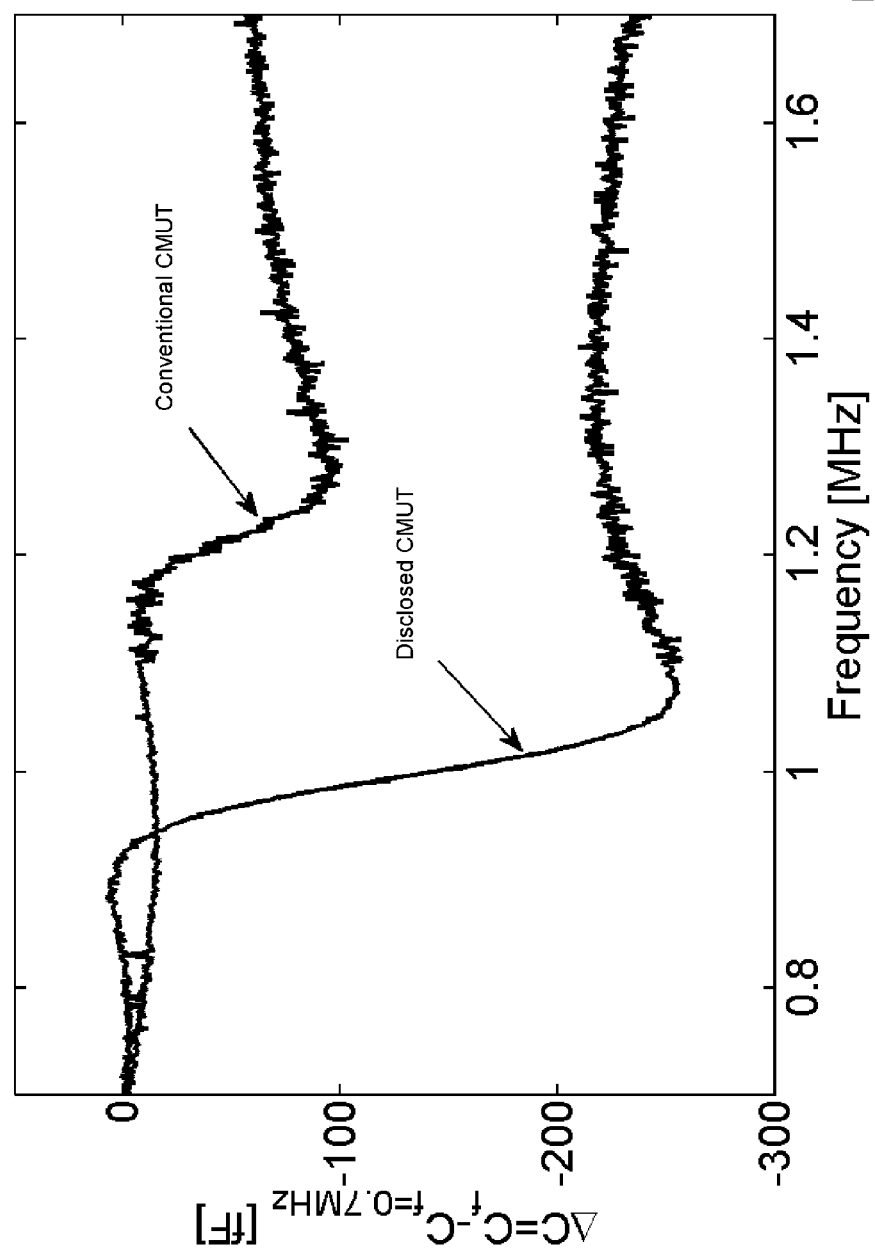
FIGS. 19B and 20A are charts comparing the change in capacitances of an example of the disclosed CMUTs with that of a conventional CMUT.

FIG. 19A shows the phase change of the example disclosed CMUT and conventional CMUT at a DC bias voltage of 25 V superimposed by a 50 mV AC signal. It can be seen from FIG. 19A that the example disclosed CMUT exhibited a larger phase change at the same bias voltage compared to the conventional CMUT. FIG. 19B shows the change in capacitances in the example disclosed CMUT and conventional CMUT, measured close to their resonant frequencies (1.0 and 1.2 MHz, respectively) with a DC bias voltage of 25 V. Both devices were biased at 25 $V_{DC}$. It can be seen that the example disclosed CMUT showed a higher capacitance variation close to the resonant frequency than the CMUT, which is consistent with the impedance measurement results.

Figure 20A:
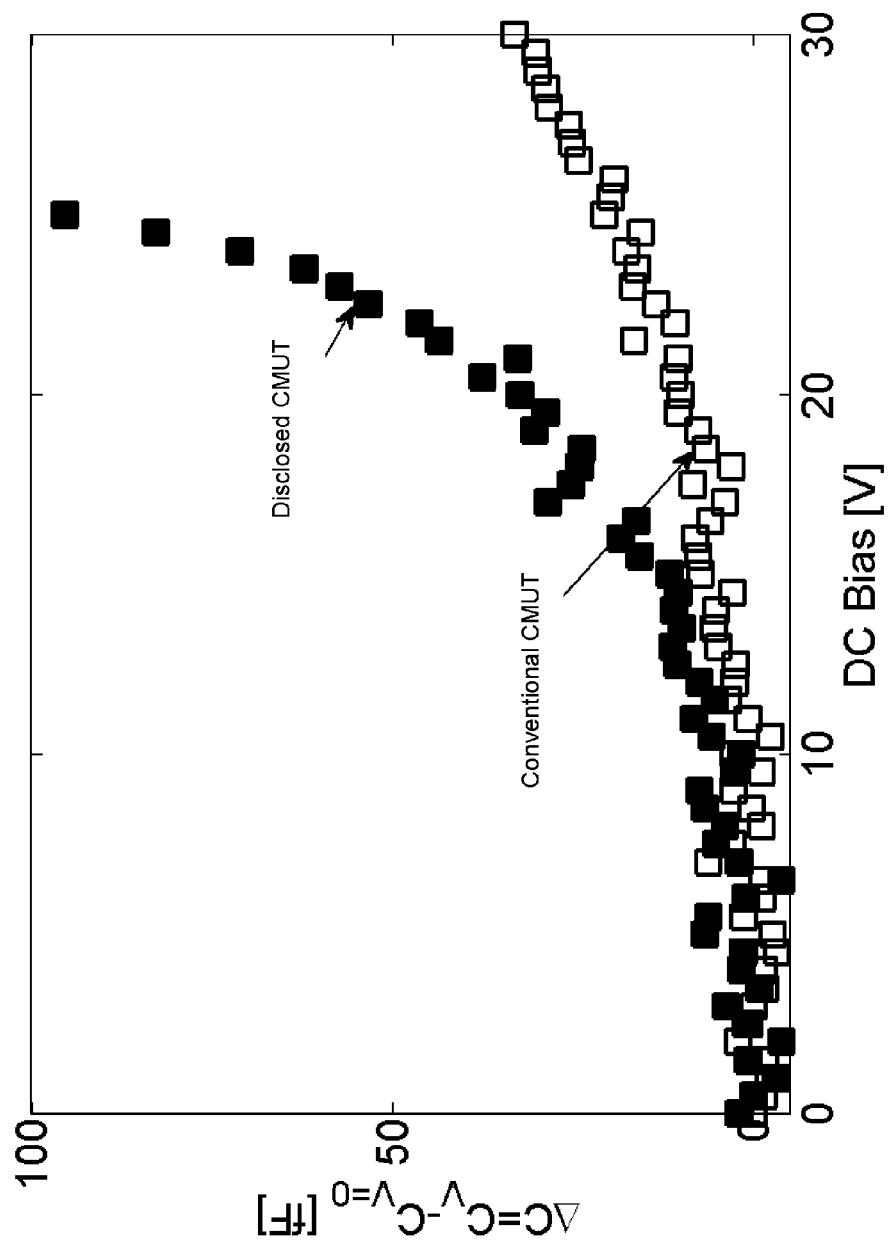
Figure 20B:
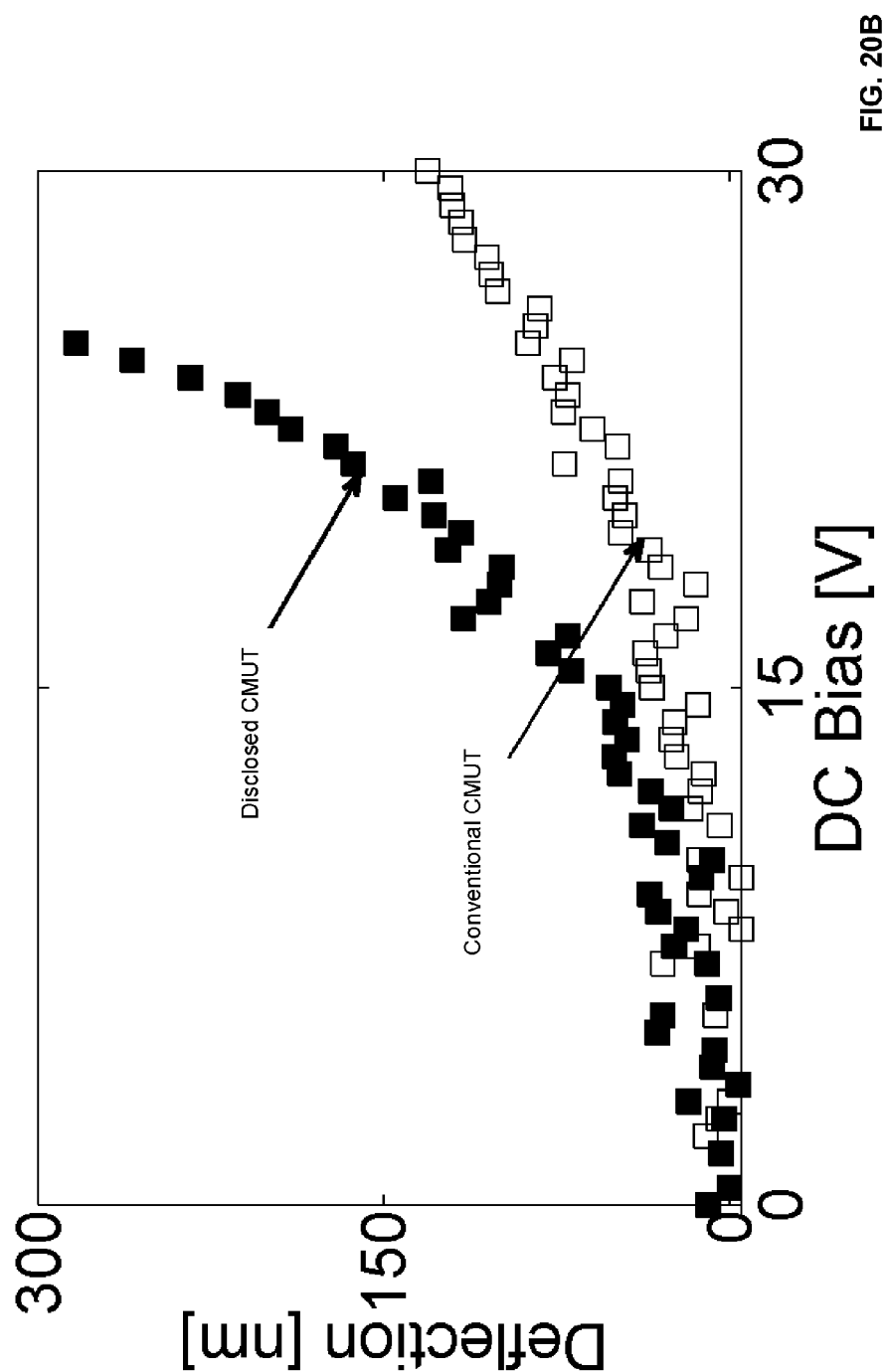
FIG. 20B is chart comparing the derived membrane deflections of an example of the disclosed CMUTs with that of a conventional CMUT.

Capacitance measurements in the example disclosed CMUT and conventional CMUT were performed as a function of applied DC bias at a low frequency of 100 kHz for a DC voltage ranging from 0 V to 25 V and 30 V, respectively, close to the transducers' collapse voltages. These single frequency capacitance measurement results and the associate derived deflection curves are shown in FIGS. 20A and 20B, respectively. It can be seen that by increasing the DC voltage, the example disclosed CMUT capacitance increased and diverged from the conventional CMUT capacitance curve. This was found to be more pronounced close to the device pull down voltage, where the deflectable membranes may be at their optimum positions.

Assuming a simple parallel plate model, C=EA/d, the effective cavity height and therefore total membrane deflection can be approximated from the capacitance measurements. In FIG. 20B, the equivalent (center) membrane displacement is shown. At a 25 $V_{DC}$, the total membrane deflection of the example disclosed CMUT was found to be about 280 nm, while the deflection was only about 85 nm for the conventional CMUT device. This may confirm once again the greater membrane displacement with the disclosed CMUT. From FIGS. 20A and 20B it can also be observed that the same deflection amplitude for both devices is achieved at a much lower voltage in the example disclosed CMUT device. Therefore, in addition to possible improvement of the transducer properties, employing the disclosed CMUT design may also help to reduce the required driving voltage.

Example 3

This example study examines examples of the disclosed CMUTs formed with curved or flat anchor configurations, such as described above with respect to FIGS. 21A and 21B.

Figure 22B:
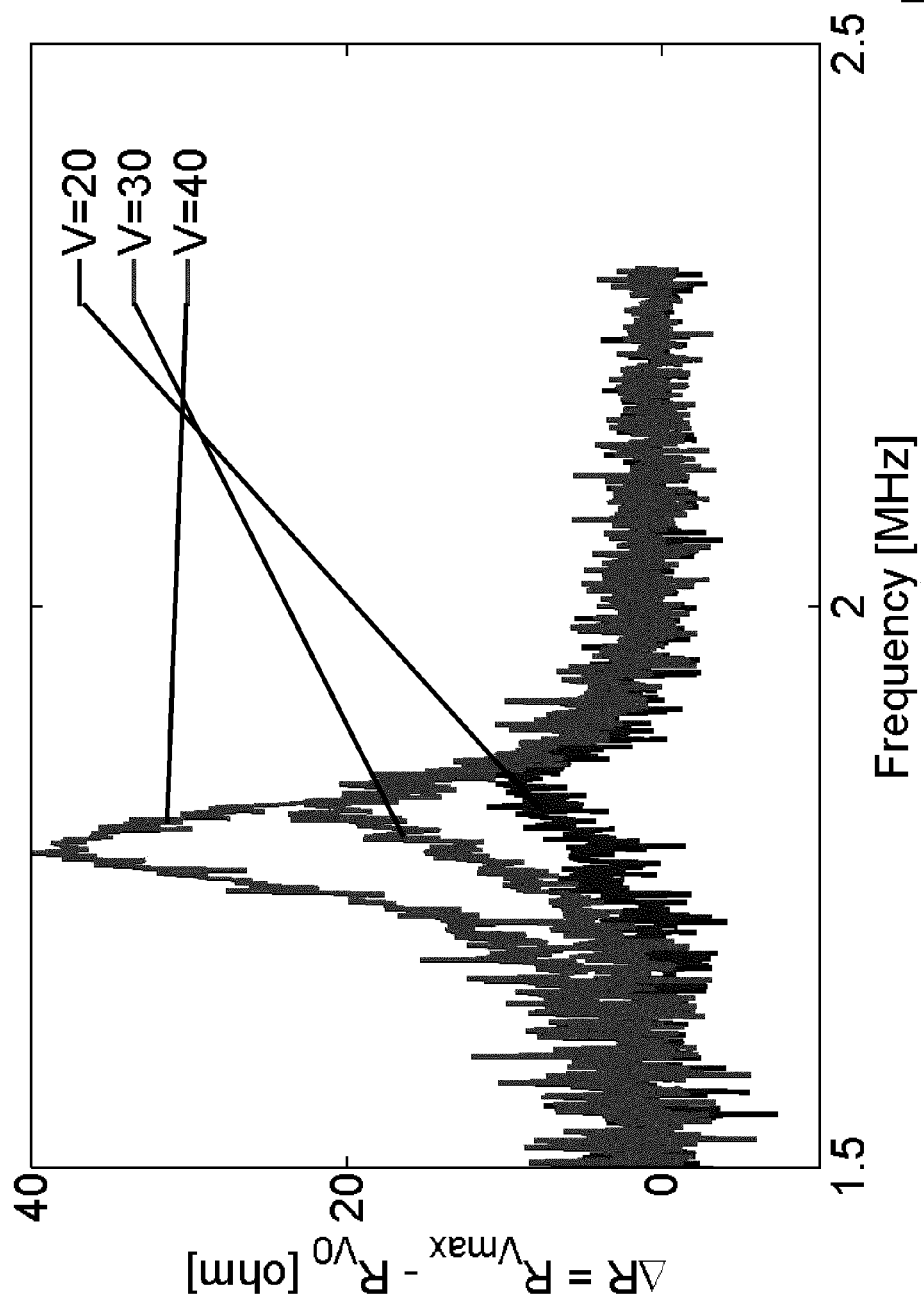
Figure 23:
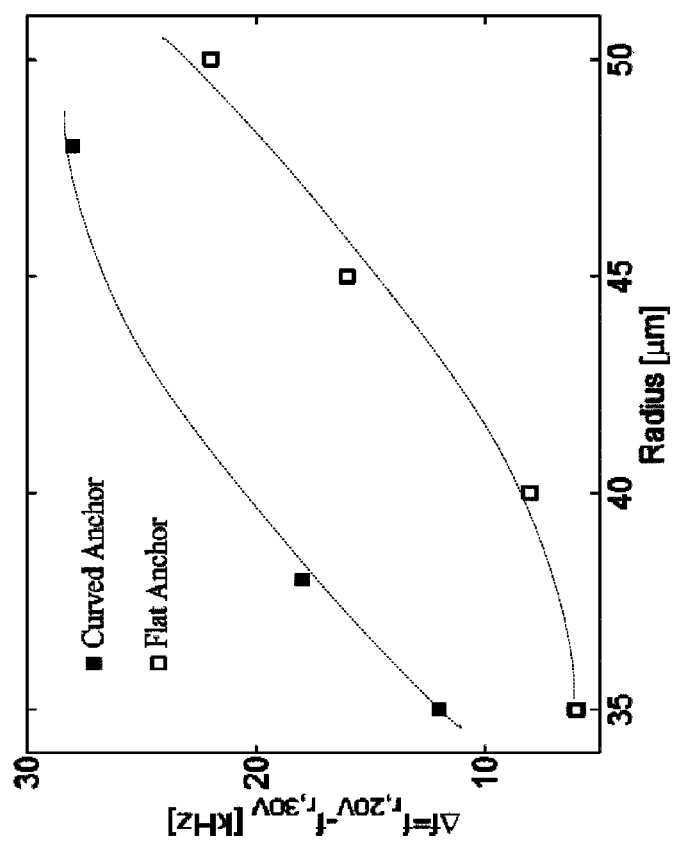
FIG. 23 is a chart showing resonant frequency shifts for examples of the disclosed CMUTs, having curved and flat anchor configurations.

Mechanical resonant frequencies of the example transducers were measured in air using an Agilent Precision Impedance Analyzer 4294A at different bias voltages. In FIGS. 22A and 22B, the real part of the impedances are shown for 48 and 50 µm radius examples of the disclosed CMUT devices with curved- and flat-anchor configurations, respectively. The resonant frequencies at a DC voltage of 40 V were found to be roughly equivalent at 1.9 MHz and 1.85 MHz for example disclosed CMUTs with curved- and flat anchor configurations, respectively. The resonant frequency shifts of these transducers associated with the spring softening effect were measured for DC voltages of 20, 30 and 40V, with a membrane radius of 48 µm for the curved anchored device and a membrane radius of 50 µm for the flat anchored device. In FIG. 23, the resonant frequency shifts for a DC voltage change of 20 to 30 V are presented for both the curved- and flat-anchor configuration devices with a membrane radius ranging from 35 to 50 µm. The example disclosed CMUTs with curved anchor configuration were found to exhibit a larger resonant frequency shift compared to the example disclosed CMUTs with flat anchor configurations. This may indicate a smaller membrane spring constant in the curved anchor configurations compared to the flat anchor configurations, for the same effective membrane radius.

A comparison was made between a 55 µm radius example of the disclosed CMUT and a conventional CMUT fabricated with the same technique and membrane radius. Resonant frequency measurements were performed and the transducers spring constants were extracted from the shift in the device resonant frequencies. The results indicated that the example disclosed CMUT underwent a larger spring constant variation, relative to the conventional device, when the DC bias voltage increases from 20V to 40V, 12.6% compared to 7.6% for the conventional device. The different amount of spring constant variation may be a result of smaller effective cavity height, caused by deflection of the two membranes, instead of just the single membrane in the conventional capacitive transducers.

The results of this example study also indicated that, in examples of the disclosed CMUTs, anchoring a membrane directly on the substrate, which results in a curved anchor configuration (e.g., as shown in FIG. 21A), showed higher resonant frequency shift for a given DC voltage change. For a given change in the bias voltage, it was also found that this curved anchor configuration exhibited a larger spring constant change, and higher membrane deflection compared to conventional CMUTs. This in turn may help to enhance the device sensitivity, resolution, and/or power generation capabilities of the disclosed CMUT.

Possible Advantages

In various examples and embodiments, the present disclosure may provide one or more of the following advantages over conventional CMUTs.

The disclosed CMUT may allow for the omission of an insulator layer between membranes, for example between a bottom static membrane and its immediately adjacent membrane. This may avoid a build-up of charge across the insulator layer, as may occur in conventional CMUTs. The omission of the insulator layer may also allow a lower bias voltage to be used in order to achieve a desired amount of displacement. By permitting the use of a lower bias voltage, the disclosed CMUT may allow for power savings and/or increased safety.

The use of lower bias voltage may also allow the disclosed CMUT to be used in applications where conventional CMUTs may be limited by the need for high bias voltage. For example, higher bias voltages are typically required when smaller transducer devices are used (e.g., for imaging in blood vessels), which may restrict the use of conventional CMUTs (e.g., due to power and/or safety limitations). The disclosed CMUT may allow for lower bias voltages to be used, even in smaller transducer devices.

The disclosed CMUT may also enable a smaller effective gap (e.g., between the upper and middle deflectable membranes) to be achieved for a given bias voltage, compared to conventional CMUTs. This may allow for a greater sensitivity and/or better signal-to-noise ratio to be attained without requiring higher bias voltages. As illustrated in FIG. 7, for example, the disclosed CMUT may enable the use of a lower bias voltage in order to achieve a desired power output, compared to conventional CMUTs. Again, the result may be power savings and/or increased safety, similar to that described above.

Because the disclosed CMUT includes a plurality of deflectable membranes, the effective gap between membranes may be adjusted (e.g., dynamically during use or according to known or desired application) by adjusting the bias voltage. This may allow the same CMUT design to be used for different applications. For example, if the CMUT is intended for use as a pressure sensor (e.g., being pressed up against a surface such as a patient's skin), a negative bias voltage may be applied to the middle deflectable membrane in order to bias the middle deflectable membrane away from the top deflectable membrane and thus avoid the possibility of the top deflectable membrane shorting with the middle deflectable membrane. Conversely, in the same CMUT, the middle deflectable membrane may be biased towards the top deflectable membrane in other applications, in order to achieve a higher sensitivity. In contrast, for conventional CMUTs, different designs may be required to achieve such different requirements for different applications.

The inclusion of multiple deflectable membranes may also allow the disclosed CMUT to continue functioning even when the upper deflectable membrane is obstructed from vibrating (e.g., when the CMUT is pressed up against a surface, such as a patient's skin).

In an "inverse biasing mode", the uppermost deflectable membrane (normally biased) and the static membrane may be grounded. The transducer driving voltage may be then applied to the middle deflectable membrane, which is sandwiched between the two grounded membranes, completely isolated the middle membrane from the surrounding media. It has been found experimentally that the disclosed CMUT in this "inverse biasing" mode may suffer little or no performance degradation. This arrangement may be beneficial in medical applications, for example, where there is a desire not to have the imaging object (e.g., a patient's body) subjected to any applied bias. Thus, using this isolated biased membrane configuration made possible by the disclosed CMUT, the present disclosure may be useful for imaging purposes where safety is a concern.

Different voltages and/or frequencies may be applied to different deflectable membranes in the disclosed CMUT. As well, each deflectable membrane in the disclosed CMUT may be made of different or same materials, and may have different or same dimensions (e.g., thicknesses). Thus, there may be customization of timing, beam patterns, sensitivity and/or power generation, for example.

The disclosed CMUT may be suitable for use in various applications and devices in which conventional CMUTs may be used. The disclosed CMUT may be usable in both send and receive mode. For example, a device may include two or more of the disclosed CMUTs arranged side-by-side or in an array, with some CMUTs in send mode while others are in receive mode, in order to achieve simultaneous sending and receiving in a single device. The disclosed CMUT may also enable beam steering.

Any suitable materials and techniques may be used in fabrication of the disclosed CMUT. For example, materials and techniques suitable for fabrication of conventional CMUTs may also be suitable for fabrication of the disclosed CMUT.

The disclosed CMUT may be used (e.g., in an array of a plurality of CMUTs) in an imaging transducer, or a range sensor, among other possible applications.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. Also, while the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. The subject matter described herein intends to cover and embrace all suitable changes in technology. All references mentioned are hereby incorporated by reference in their entirety.

REFERENCES

[1] T. L. Szabo, Diagnostic Ultrasound Imaging—Inside Out, Elsver Academic Press, 2004.
[2] G. Thomas, D. Flores-Tapia, S. Pistorius, N. Fernando, "Synthetic aperture ultrasound imaging of XLPE insulation of underground power cables", IEEE Electrical Insulation Magazine, vol. 26, no. 34, pp. 24-34, 2010.
[3] M. Crocco, P. Pellegretti, C. Sciallero A. Trucco, "Combining multi pulse excitation and chirp coding in contrast-enhanced ultrasound imaging", Measurements Science and Technology, vol. 20, 104017, 2009.
[4] A. S. Logan, J. T. W. Yeow, "Fabricating capacitive micromachined ultrasonic transducers with a novel silicon-nitride-based wafer bonding process", IEEE Transactions on Ultrasonics, and Frequency Control, vol. 56, no. 5, pp. 1074-1084, 2009.
[5] B. T. Khuri-Yakub, O. Oralkon, M. Kupnik, "Next-gen ultrasound", IEEE Spectrum, vol. 46, no. 5, pp. 44-54, 2009.
[6] P. Zhang, G. Fitzpatric, W. Moussa, R. J. Zemp, "CMUTs with improved electrical safety & minimal dielectric surface charging", in Proc. IEEE Ultrasonics Symposium, San Diego, Calif., pp. 1881-1885, 2010.
[7] T. A. Emadi, G. Thomas, S. Pistorius, D. A. Buchanan, "Design and analysis of a wide bandwidth immersion MEMS transducer array for fault detection in power cables," IEEE Sensors, Taipei, Taiwan, October 2012.
[8] T. A. Emadi, G. Thomas, S. Pistorius, D. A. Buchanan, "Capacitive micromachined ultrasonic transducer array with pencil beam shape and wide range beam steering," The 26th Conference on Solid-State Transducers, Eurosensors, Krakow, Poland, September 2012.
[9] O. Oralkon, A. S. Ergun, J. A. Jhonson, M. Karaman, U. Demirci, K. Kaviani, T. H. Lee, B. T. Khuri-Yahub, "Capacitive micromachined ultrasonic transducers: next-generation arrays for acoustic imaging?", IEEE Transaction on Ultrasonics, Ferroelectrics, and Frequency Control, vol. 49, no. 11, pp. 1596-1610, 2002.
[10] W. You, E. Cretu, R. Rohling, M. Cai, "Tiltable ultrasonic transducers: concept, beamforming methods and simulation," IEEE Sensors Journal, vol. 11, no. 10, pp. 2286-2300, 2011.
[11] L. L. Liu, O. M. Mukdadi, C. F. Herrmann, R. A. Saravanan, J. R. Hertzberg, S. M. George, V. M. Bright, R. Shandas, "A novel method for fabrication capacitive micromachined ultrasonic transducers with ultra-thin membranes," IEEE Ultrasonics Symposium, pp. 497-500, 2004.
[12] MEMSCAP, www.memscap.com/products/mumps/polymumps
[13] COMSOL, http://www.comsol.com/

The invention claimed is:

1. A capacitive micromachined ultrasonic transducer (CMUT) comprising:
at least two deflectable membranes adjacent to each other;
each of the at least two deflectable membranes being spaced from each other over an entire area of each deflectable membrane, in absence of any biasing voltage;
the at least two deflectable membranes contributing to and/or being responsive to receive or transmit an ultrasonic signal; and
spacing between the at least two deflectable membranes being adjustable through application of a voltage to cause deflection of at least one of the deflectable membranes, to affect the receive/transmit properties of the CMUT.

2. The CMUT of claim 1 further comprising a static membrane spaced apart from the at least two deflectable membranes.

3. The CMUT of claim 1 further comprising at least one electrical contact permitting electrical connection with at least a signal source, the at least one electrical contact being in electrical connection with at least one deflectable membrane.

4. The CMUT of claim 3 further comprising at least a second electrical contact permitting electrical connection with a ground.

5. The CMUT of claim 1 further comprising at least one support for spacing the at least two deflectable membranes from each other.

6. The CMUT of claim 5 further comprising a substrate supporting the at least one support.

7. The CMUT of claim 1 further comprising a substrate supporting at least one deflectable membrane.

8. The CMUT of claim 7 wherein the at least one deflectable membrane is anchored to the substrate.

9. The CMUT of claim 7 wherein the at least one deflectable membrane is anchored to the substrate via an intermediary support.

10. The CMUT of claim 1 wherein there are two deflectable membranes.

11. The CMUT of claim 1 further comprising an insulator positioned to insulate at least one of the deflectable membranes from at least one other static or deflectable membrane.

12. The CMUT of claim 1 wherein the CMUT is fabricated using a sacrificial layer technique.

13. The CMUT of claim 1 wherein the CMUT is fabricated using a bonding process.

14. A method of operating the CMUT of claim 1 comprising:
   applying a respective DC biasing voltage to at least one of the deflectable membranes to space the at least one deflectable membrane at an initial separation from another deflectable membrane; and
   applying a respective AC driving voltage to at least a same or different one of the deflectable membrane.

15. The method of claim 14, further comprising:
   applying respective DC biasing voltages to each of the deflectable membranes to space the deflectable membranes at initial separations from each other; and
   applying respective AC driving voltages to each of the deflectable membranes.

16. The method of claim 14 wherein the DC biasing voltage applied to at least one deflectable membrane is different from the DC biasing voltage applied to at least another one deflectable membrane.

17. The method of claim 14 wherein the AC driving voltage applied to at least one deflectable membrane is different from the AC driving voltage applied to at least another one deflectable membrane.

18. The method of claim 14 wherein the respective DC biasing voltages are selected to space the deflectable membranes at a selected separation from each other.

19. A method of operating the CMUT of claim 1 comprising:
   grounding an outermost of the deflectable membranes, the outermost deflectable being defined as the deflectable membrane contactable by an object external to the CMUT; and
   applying a DC biasing voltage and an AC driving voltage to at least one other deflectable membrane.

20. An imaging transducer comprising an array of a plurality of the CMUT of claim 1.

* * * * *